(12) United States Patent
Guthart et al.

(10) Patent No.: US 9,232,984 B2
(45) Date of Patent: Jan. 12, 2016

(54) REAL-TIME GENERATION OF THREE-DIMENSIONAL ULTRASOUND IMAGE USING A TWO-DIMENSIONAL ULTRASOUND TRANSDUCER IN A ROBOTIC SYSTEM

(75) Inventors: Gary S. Guthart, Los Altos, CA (US); Gunter D. Niemeyer, Mountain View, CA (US); Robert G. Younge, Portola Valley, CA (US); J. Kenneth Salisbury, Mountain View, CA (US); Thomas G. Cooper, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 12/943,754

(22) Filed: Nov. 10, 2010

(65) Prior Publication Data

US 2011/0105898 A1 May 5, 2011

Related U.S. Application Data

(60) Division of application No. 11/093,372, filed on Mar. 30, 2005, now Pat. No. 8,944,070, which is a continuation-in-part of application No. 10/314,001, filed on Dec. 5, 2002, now Pat. No. 7,107,090, which (Continued)

(51) Int. Cl.
*A61B 17/00* (2006.01)
*A61B 19/00* (2006.01)

(Continued)

(52) U.S. Cl.
CPC ............... *A61B 19/5244* (2013.01); *A61B 1/04* (2013.01); *A61B 8/12* (2013.01); *A61B 8/4218* (2013.01); *A61B 17/00234* (2013.01); *A61B 19/22* (2013.01); *A61B 19/2203* (2013.01); *A61B 19/52* (2013.01); *A61B 1/0005* (2013.01);

(Continued)

(58) Field of Classification Search
CPC ................. A61B 19/2203; A61B 1/04; G06T 2207/10068
USPC ............................................................ 606/1
See application file for complete search history.

(56) References Cited

U.S. PATENT DOCUMENTS

| | | |
|---|---|---|
| 3,628,535 A | 12/1971 | Ostrowsky et al. |
| 3,818,284 A | 6/1974 | DeVersterre et al. |

(Continued)

FOREIGN PATENT DOCUMENTS

| | | |
|---|---|---|
| EP | 514584 A2 | 11/1992 |
| EP | 0646358 A1 | 4/1995 |

(Continued)

OTHER PUBLICATIONS

Adams, Ludwig et al., "Computer-Assisted Surgery," IEEE Computer Graphics & Applications, May 1990, pp. 43-52, vol. 10—Issue 3, IEEE Computer Society Press.

(Continued)

*Primary Examiner* — Aaron Roane

(57) ABSTRACT

Systems and methods for performing robotically-assisted surgical procedures on a patient enable an image display device to provide an operator with auxiliary information related to the surgical procedure, in addition to providing an image of the surgical site itself. The systems and methods allow an operator to selectively access and reference auxiliary information on the image display device during the performance of a surgical procedure.

5 Claims, 12 Drawing Sheets

Related U.S. Application Data is a continuation of application No. 09/464,455, filed on Dec. 14, 1999, now Pat. No. 6,522,906, which is a continuation-in-part of application No. 09/457,406, filed on Dec. 7, 1999, now Pat. No. 6,799,065, said application No. 11/093,372 is a continuation-in-part of application No. 10/644,406, filed on Aug. 19, 2003, now abandoned, which is a continuation of application No. 10/163,626, filed on Jun. 5, 2002, now Pat. No. 6,671,581, which is a continuation of application No. 09/373,678, filed on Aug. 13, 1999, now Pat. No. 6,424,885.

(60) Provisional application No. 60/128,160, filed on Apr. 7, 1999.

(51) Int. Cl.
*A61B 1/04* (2006.01)
*A61B 8/12* (2006.01)
*A61B 1/00* (2006.01)
*A61B 8/00* (2006.01)
*A61B 18/20* (2006.01)
*A61B 1/313* (2006.01)

(52) U.S. Cl.
CPC .......... *A61B1/00045* (2013.01); *A61B 1/3132* (2013.01); *A61B 8/4245* (2013.01); *A61B 18/20* (2013.01); *A61B 19/5212* (2013.01); *A61B 2019/223* (2013.01); *A61B 2019/2223* (2013.01); *A61B 2019/2234* (2013.01); *A61B 2019/265* (2013.01); *A61B 2019/301* (2013.01); *A61B 2019/464* (2013.01); *A61B 2019/465* (2013.01); *A61B 2019/466* (2013.01); *A61B 2019/4836* (2013.01); *A61B 2019/507* (2013.01)

(56) References Cited

U.S. PATENT DOCUMENTS

| | | |
|---|---|---|
| 3,905,215 A | 9/1975 | Wright |
| 3,923,166 A | 12/1975 | Fletcher et al. |
| 4,150,326 A | 4/1979 | Engelberger et al. |
| 4,349,837 A | 9/1982 | Hinds |
| 4,577,621 A | 3/1986 | Patel |
| 4,588,348 A | 5/1986 | Beni et al. |
| 4,644,237 A | 2/1987 | Frushour et al. |
| 4,672,963 A | 6/1987 | Barken |
| 4,722,056 A | 1/1988 | Roberts et al. |
| 4,762,455 A | 8/1988 | Coughlan et al. |
| 4,762,456 A | 8/1988 | Nelson |
| 4,791,934 A | 12/1988 | Brunnett |
| 4,815,450 A | 3/1989 | Patel |
| 4,831,549 A | 5/1989 | Red et al. |
| 4,833,383 A | 5/1989 | Skarr et al. |
| 4,837,703 A | 6/1989 | Kakazu et al. |
| 4,837,734 A | 6/1989 | Ichikawa et al. |
| 4,839,838 A | 6/1989 | LaBiche et al. |
| 4,853,874 A | 8/1989 | Iwamoto et al. |
| 4,858,149 A | 8/1989 | Quarendon |
| 4,860,215 A | 8/1989 | Seraji |
| 4,863,133 A | 9/1989 | Bonnell |
| 4,942,539 A | 7/1990 | McGee et al. |
| 4,979,949 A | 12/1990 | Matsen, III |
| 4,984,157 A | 1/1991 | Cline et al. |
| 4,989,253 A | 1/1991 | Liang et al. |
| 5,046,022 A | 9/1991 | Conway et al. |
| 5,053,976 A | 10/1991 | Nose et al. |
| 5,079,699 A | 1/1992 | Tuy et al. |
| 5,086,401 A | 2/1992 | Glassman et al. |
| 5,098,426 A | 3/1992 | Sklar et al. |
| 5,099,846 A | 3/1992 | Hardy |
| 5,142,930 A | 9/1992 | Allen et al. |
| 5,170,347 A | 12/1992 | Tuy et al. |
| 5,174,276 A | 12/1992 | Crockard |
| 5,176,702 A | 1/1993 | Bales et al. |
| 5,182,641 A | 1/1993 | Diner et al. |
| 5,184,009 A | 2/1993 | Wright et al. |
| 5,184,601 A | 2/1993 | Putman |
| 5,187,796 A | 2/1993 | Wang et al. |
| 5,217,003 A | 6/1993 | Wilk |
| 5,230,338 A | 7/1993 | Allen et al. |
| 5,230,623 A | 7/1993 | Guthrie et al. |
| 5,235,510 A | 8/1993 | Yamada et al. |
| 5,239,246 A | 8/1993 | Kim |
| 5,251,127 A | 10/1993 | Raab |
| 5,251,611 A | 10/1993 | Zehel et al. |
| 5,257,203 A | 10/1993 | Riley et al. |
| 5,261,404 A | 11/1993 | Mick et al. |
| 5,266,875 A | 11/1993 | Slotine et al. |
| 5,279,309 A | 1/1994 | Taylor et al. |
| 5,299,288 A | 3/1994 | Glassman et al. |
| 5,313,306 A | 5/1994 | Kuban et al. |
| 5,321,353 A | 6/1994 | Furness |
| 5,337,733 A | 8/1994 | Bauerfeind et al. |
| 5,341,950 A | 8/1994 | Sinz |
| 5,343,385 A | 8/1994 | Joskowicz et al. |
| 5,368,015 A | 11/1994 | Wilk |
| 5,368,428 A | 11/1994 | Hussey et al. |
| 5,382,885 A | 1/1995 | Salcudean et al. |
| 5,397,323 A | 3/1995 | Taylor et al. |
| 5,402,801 A | 4/1995 | Taylor |
| 5,408,409 A | 4/1995 | Glassman et al. |
| 5,417,210 A | 5/1995 | Funda et al. |
| 5,430,643 A | 7/1995 | Seraji |
| 5,445,166 A | 8/1995 | Taylor |
| 5,454,827 A | 10/1995 | Aust et al. |
| 5,474,571 A | 12/1995 | Lang |
| 5,482,029 A | 1/1996 | Sekiguchi et al. |
| 5,493,595 A | 2/1996 | Schoolman |
| 5,503,320 A | 4/1996 | Webster et al. |
| 5,515,478 A | 5/1996 | Wang |
| 5,524,180 A | 6/1996 | Wang et al. |
| 5,528,955 A | 6/1996 | Hannaford et al. |
| 5,531,742 A | 7/1996 | Barken |
| 5,551,432 A | 9/1996 | Iezzi |
| 5,553,198 A | 9/1996 | Wang et al. |
| 5,572,999 A | 11/1996 | Funda et al. |
| 5,601,549 A * | 2/1997 | Miyagi ........................... 606/4 |
| 5,617,858 A | 4/1997 | Taverna et al. |
| 5,624,398 A | 4/1997 | Smith et al. |
| 5,631,973 A | 5/1997 | Green |
| 5,638,819 A | 6/1997 | Manwaring et al. |
| 5,657,429 A | 8/1997 | Wang et al. |
| 5,695,500 A | 12/1997 | Taylor et al. |
| 5,704,897 A | 1/1998 | Truppe |
| 5,715,729 A | 2/1998 | Toyama et al. |
| 5,737,500 A | 4/1998 | Seraji et al. |
| 5,748,767 A | 5/1998 | Raab |
| 5,749,362 A | 5/1998 | Funda et al. |
| 5,754,741 A | 5/1998 | Wang et al. |
| 5,755,725 A | 5/1998 | Druais |
| 5,759,151 A | 6/1998 | Sturges |
| 5,759,153 A | 6/1998 | Webler et al. |
| 5,762,458 A | 6/1998 | Wang et al. |
| 5,765,561 A | 6/1998 | Chen et al. |
| 5,784,542 A | 7/1998 | Ohm et al. |
| 5,788,688 A | 8/1998 | Bauer et al. |
| 5,791,231 A | 8/1998 | Cohn et al. |
| 5,792,135 A | 8/1998 | Madhani et al. |
| 5,797,849 A | 8/1998 | Vesely et al. |
| 5,797,900 A | 8/1998 | Madhani et al. |
| 5,807,377 A | 9/1998 | Madhani et al. |
| 5,808,665 A | 9/1998 | Green |
| 5,810,008 A | 9/1998 | Dekel et al. |
| 5,810,880 A | 9/1998 | Jensen et al. |
| 5,814,038 A | 9/1998 | Jensen et al. |
| 5,815,640 A | 9/1998 | Wang et al. |
| 5,817,022 A | 10/1998 | Vesely |
| 5,820,545 A | 10/1998 | Arbter et al. |
| 5,820,623 A | 10/1998 | Ng |
| 5,831,408 A | 11/1998 | Jacobus et al. |

(56) References Cited

U.S. PATENT DOCUMENTS

| | | |
|---|---|---|
| 5,835,693 A | 11/1998 | Lynch et al. |
| 5,836,880 A | 11/1998 | Pratt |
| 5,841,950 A | 11/1998 | Wang et al. |
| 5,842,473 A | 12/1998 | Fenster et al. |
| 5,842,993 A | 12/1998 | Eichelberger et al. |
| 5,853,367 A | 12/1998 | Chalek et al. |
| 5,855,553 A | 1/1999 | Tajima et al. |
| 5,855,583 A | 1/1999 | Wang et al. |
| 5,859,934 A | 1/1999 | Green |
| 5,876,325 A | 3/1999 | Mizuno et al. |
| 5,877,819 A | 3/1999 | Branson |
| 5,878,193 A | 3/1999 | Wang et al. |
| 5,887,121 A | 3/1999 | Funda et al. |
| 5,907,664 A | 5/1999 | Wang et al. |
| 5,911,036 A | 6/1999 | Wright et al. |
| 5,931,832 A | 8/1999 | Jensen |
| 5,938,678 A | 8/1999 | Zirps et al. |
| 5,950,629 A | 9/1999 | Taylor et al. |
| 5,964,707 A | 10/1999 | Fenster et al. |
| 5,971,976 A | 10/1999 | Wang et al. |
| 5,980,460 A | 11/1999 | Ostensent et al. |
| 5,980,461 A | 11/1999 | Rajan |
| 5,987,591 A | 11/1999 | Jyumonji |
| 5,993,390 A | 11/1999 | Savord |
| 5,993,391 A | 11/1999 | Kamiyama et al. |
| 6,019,724 A | 2/2000 | Gronningsaeter et al. |
| 6,059,718 A | 5/2000 | Taniguchi et al. |
| 6,063,095 A | 5/2000 | Wang et al. |
| 6,083,170 A | 7/2000 | Ben-Haim |
| 6,084,371 A | 7/2000 | Kress et al. |
| 6,096,025 A | 8/2000 | Borders |
| 6,115,053 A | 9/2000 | Perlin |
| 6,120,433 A | 9/2000 | Mizuno et al. |
| 6,129,670 A | 10/2000 | Burdette et al. |
| 6,184,868 B1 | 2/2001 | Shahoian et al. |
| 6,196,081 B1 | 3/2001 | Yau |
| 6,201,984 B1 | 3/2001 | Funda et al. |
| 6,204,620 B1 | 3/2001 | McGee et al. |
| 6,224,542 B1 | 5/2001 | Chang et al. |
| 6,226,566 B1 | 5/2001 | Funda et al. |
| 6,241,725 B1 | 6/2001 | Cosman |
| 6,243,624 B1 | 6/2001 | Wu et al. |
| 6,246,200 B1 | 6/2001 | Blumenkranz et al. |
| 6,256,529 B1 | 7/2001 | Holupka et al. |
| 6,270,453 B1 | 8/2001 | Sakai |
| 6,292,712 B1 | 9/2001 | Bullen |
| 6,307,285 B1 | 10/2001 | Delson et al. |
| 6,312,435 B1 | 11/2001 | Wallace et al. |
| 6,325,808 B1 | 12/2001 | Bernard et al. |
| 6,330,837 B1 | 12/2001 | Charles et al. |
| 6,331,181 B1 | 12/2001 | Tierney et al. |
| 6,342,889 B1 | 1/2002 | Callahan |
| 6,371,909 B1 | 4/2002 | Hoeg et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,402,737 B1 | 6/2002 | Tajima et al. |
| 6,424,885 B1 | 7/2002 | Niemeyer et al. |
| 6,425,865 B1 | 7/2002 | Salcudean et al. |
| 6,436,107 B1 | 8/2002 | Wang et al. |
| 6,442,417 B1 | 8/2002 | Shahidi et al. |
| 6,456,901 B1 | 9/2002 | Xi et al. |
| 6,459,926 B1 | 10/2002 | Nowlin et al. |
| 6,468,265 B1 | 10/2002 | Evans et al. |
| 6,493,608 B1 | 12/2002 | Niemeyer |
| 6,522,906 B1 | 2/2003 | Salisbury, Jr. et al. |
| 6,547,782 B1 | 4/2003 | Taylor |
| 6,550,757 B2 | 4/2003 | Sesek |
| 6,569,084 B1 | 5/2003 | Mizuno et al. |
| 6,574,355 B2 | 6/2003 | Green |
| 6,594,522 B1 | 7/2003 | Korenaga |
| 6,594,552 B1 | 7/2003 | Nowlin et al. |
| 6,599,247 B1 | 7/2003 | Stetten |
| 6,602,185 B1 | 8/2003 | Uchikubo |
| 6,642,836 B1 | 11/2003 | Wang et al. |
| 6,643,563 B2 | 11/2003 | Hosek et al. |
| 6,645,196 B1 | 11/2003 | Nixon et al. |
| 6,648,816 B2 | 11/2003 | Irion et al. |
| 6,654,031 B1 | 11/2003 | Ito et al. |
| 6,659,939 B2 | 12/2003 | Moll et al. |
| 6,671,581 B2 | 12/2003 | Niemeyer et al. |
| 6,676,669 B2 | 1/2004 | Charles et al. |
| 6,699,177 B1 | 3/2004 | Wang et al. |
| 6,714,839 B2 | 3/2004 | Salisbury et al. |
| 6,770,081 B1 | 8/2004 | Cooper et al. |
| 6,786,896 B1 | 9/2004 | Madhani et al. |
| 6,799,065 B1 | 9/2004 | Niemeyer |
| 6,837,883 B2 | 1/2005 | Moll et al. |
| 6,847,922 B1 | 1/2005 | Wampler, II |
| 6,852,107 B2 | 2/2005 | Wang et al. |
| 6,876,891 B1 | 4/2005 | Schuler et al. |
| 6,926,709 B2 | 8/2005 | Bieger et al. |
| 6,960,162 B2 | 11/2005 | Saadat et al. |
| 6,984,203 B2 | 1/2006 | Tartaglia et al. |
| 6,991,627 B2 | 1/2006 | Madhani et al. |
| 7,041,053 B2 | 5/2006 | Miyake |
| 7,107,090 B2 | 9/2006 | Salisbury et al. |
| 7,107,124 B2 | 9/2006 | Green |
| 7,144,367 B2 | 12/2006 | Chen et al. |
| 7,155,315 B2 | 12/2006 | Niemeyer et al. |
| 7,155,316 B2 | 12/2006 | Sutherland et al. |
| 7,181,315 B2 | 2/2007 | Watanabe et al. |
| 7,194,118 B1 | 3/2007 | Harris et al. |
| 7,413,565 B2 | 8/2008 | Wang et al. |
| 7,491,198 B2 | 2/2009 | Kockro |
| 7,574,250 B2 | 8/2009 | Niemeyer |
| 7,725,214 B2 | 5/2010 | Diolaiti |
| 7,806,891 B2 | 10/2010 | Nowlin et al. |
| 7,819,859 B2 | 10/2010 | Prisco et al. |
| 7,963,913 B2 | 6/2011 | Devengenzo et al. |
| 7,979,157 B2 | 7/2011 | Anvari |
| 7,996,110 B2 | 8/2011 | Lipow et al. |
| 7,998,058 B2 | 8/2011 | Kura et al. |
| 8,062,288 B2 | 11/2011 | Cooper et al. |
| 8,108,072 B2 | 1/2012 | Zhao et al. |
| 8,120,301 B2 | 2/2012 | Goldberg et al. |
| 8,130,907 B2 | 3/2012 | Maurer, Jr. et al. |
| 8,155,479 B2 | 4/2012 | Hoffman et al. |
| 8,170,716 B2 | 5/2012 | Coste-Maniere et al. |
| 8,221,304 B2 | 7/2012 | Shioda et al. |
| 8,256,319 B2 | 9/2012 | Cooper et al. |
| 8,306,656 B1 | 11/2012 | Schaible et al. |
| 8,315,720 B2 | 11/2012 | Mohr et al. |
| 8,335,590 B2 | 12/2012 | Costa et al. |
| 8,398,541 B2 | 3/2013 | Dimaio et al. |
| 8,554,368 B2 | 10/2013 | Fielding et al. |
| 8,620,473 B2 | 12/2013 | Diolaiti et al. |
| 8,864,652 B2 | 10/2014 | Diolaiti et al. |
| 8,903,546 B2 | 12/2014 | Diolaiti et al. |
| 8,918,211 B2 | 12/2014 | Diolaiti et al. |
| 8,944,070 B2 | 2/2015 | Guthart et al. |
| 9,084,623 B2 | 7/2015 | Gomez et al. |
| 9,089,256 B2 | 7/2015 | Tognaccini et al. |
| 9,101,397 B2 | 8/2015 | Guthart et al. |
| 2001/0035871 A1 | 11/2001 | Bieger et al. |
| 2002/0044104 A1 | 4/2002 | Friedrich et al. |
| 2002/0045905 A1 | 4/2002 | Gerbi et al. |
| 2002/0089544 A1 | 7/2002 | Jahn et al. |
| 2002/0120188 A1 | 8/2002 | Brock et al. |
| 2002/0193800 A1 | 12/2002 | Kienzle, III |
| 2003/0023347 A1 | 1/2003 | Konno et al. |
| 2003/0032878 A1 | 2/2003 | Shahidi |
| 2003/0055410 A1 | 3/2003 | Evans et al. |
| 2003/0109780 A1 | 6/2003 | Coste-Maniere et al. |
| 2003/0114730 A1 | 6/2003 | Hale et al. |
| 2003/0167103 A1 | 9/2003 | Tang et al. |
| 2003/0225479 A1 | 12/2003 | Waled |
| 2004/0024311 A1 | 2/2004 | Quaid et al. |
| 2004/0034283 A1 | 2/2004 | Quaid, III |
| 2004/0039485 A1 | 2/2004 | Niemeyer et al. |
| 2004/0046711 A1 | 3/2004 | Triebfuerst |
| 2004/0077940 A1 | 4/2004 | Kienzle et al. |
| 2004/0106916 A1 | 6/2004 | Quaid et al. |
| 2004/0189675 A1 | 9/2004 | Pretlove et al. |

(56) References Cited

U.S. PATENT DOCUMENTS

| | | |
|---|---|---|
| 2004/0225183 A1 | 11/2004 | Michlitsch et al. |
| 2004/0238732 A1 | 12/2004 | State et al. |
| 2004/0243147 A1 | 12/2004 | Lipow |
| 2004/0249508 A1 | 12/2004 | Suita et al. |
| 2004/0254679 A1 | 12/2004 | Nagasaka |
| 2005/0022158 A1 | 1/2005 | Launay et al. |
| 2005/0054895 A1 | 3/2005 | Hoeg et al. |
| 2005/0059960 A1 | 3/2005 | Simaan et al. |
| 2005/0096502 A1 | 5/2005 | Khalili |
| 2005/0113640 A1 | 5/2005 | Saadat et al. |
| 2005/0200324 A1 | 9/2005 | Guthart et al. |
| 2005/0203380 A1 | 9/2005 | Sauer et al. |
| 2005/0228365 A1 | 10/2005 | Wang et al. |
| 2005/0251113 A1 | 11/2005 | Kienzle, III |
| 2005/0267359 A1 | 12/2005 | Hussaini et al. |
| 2006/0058988 A1 | 3/2006 | Defranoux et al. |
| 2006/0142657 A1 | 6/2006 | Quaid et al. |
| 2006/0258938 A1 | 11/2006 | Hoffman et al. |
| 2006/0261770 A1 | 11/2006 | Kishi et al. |
| 2007/0013336 A1 | 1/2007 | Nowlin et al. |
| 2007/0016174 A1 | 1/2007 | Millman et al. |
| 2007/0021738 A1 | 1/2007 | Hasser et al. |
| 2007/0032906 A1 | 2/2007 | Sutherland et al. |
| 2007/0038080 A1 | 2/2007 | Salisbury, Jr. et al. |
| 2007/0060879 A1 | 3/2007 | Weitzner et al. |
| 2007/0135803 A1 | 6/2007 | Belson |
| 2007/0142968 A1 | 6/2007 | Prisco et al. |
| 2007/0144298 A1 | 6/2007 | Miller |
| 2007/0255454 A1 | 11/2007 | Dariush |
| 2007/0265491 A1 | 11/2007 | Krag et al. |
| 2007/0270650 A1 | 11/2007 | Eno et al. |
| 2007/0270685 A1 | 11/2007 | Kang et al. |
| 2007/0283970 A1 | 12/2007 | Mohr et al. |
| 2007/0287884 A1 | 12/2007 | Schena |
| 2007/0287992 A1 | 12/2007 | Diolaiti et al. |
| 2008/0004603 A1 | 1/2008 | Larkin et al. |
| 2008/0033240 A1 | 2/2008 | Hoffman et al. |
| 2008/0065099 A1 | 3/2008 | Cooper et al. |
| 2008/0065105 A1 | 3/2008 | Larkin et al. |
| 2008/0065109 A1 | 3/2008 | Larkin |
| 2008/0071291 A1 | 3/2008 | Duval et al. |
| 2008/0081992 A1 | 4/2008 | Kagermeier |
| 2008/0118115 A1 | 5/2008 | Williamson |
| 2008/0140087 A1 | 6/2008 | Barbagli |
| 2008/0161830 A1 | 7/2008 | Sutherland et al. |
| 2008/0188986 A1 | 8/2008 | Hoppe |
| 2008/0243142 A1 | 10/2008 | Gildenberg |
| 2008/0247506 A1 | 10/2008 | Maschke |
| 2008/0287963 A1 | 11/2008 | Rogers et al. |
| 2009/0012531 A1 | 1/2009 | Quaid et al. |
| 2009/0024142 A1 | 1/2009 | Ruiz Morales |
| 2009/0036902 A1 | 2/2009 | DiMaio et al. |
| 2009/0088634 A1 | 4/2009 | Zhao et al. |
| 2009/0192523 A1 | 7/2009 | Larkin et al. |
| 2009/0192524 A1 | 7/2009 | Itkowitz et al. |
| 2009/0228145 A1 | 9/2009 | Hodgson et al. |
| 2009/0248036 A1 | 10/2009 | Hoffman et al. |
| 2009/0259105 A1 | 10/2009 | Miyano et al. |
| 2009/0326318 A1 | 12/2009 | Tognaccini et al. |
| 2009/0326552 A1 | 12/2009 | Diolaiti |
| 2009/0326553 A1 | 12/2009 | Mustufa et al. |
| 2009/0326711 A1 | 12/2009 | Chang et al. |
| 2010/0004505 A1 | 1/2010 | Umemoto et al. |
| 2010/0036198 A1 | 2/2010 | Tacchino et al. |
| 2010/0106356 A1 | 4/2010 | Trepagnier et al. |
| 2010/0198232 A1 | 8/2010 | Diolaiti |
| 2010/0249657 A1 | 9/2010 | Nycz et al. |
| 2010/0317965 A1 | 12/2010 | Itkowitz et al. |
| 2010/0331856 A1 | 12/2010 | Carlson et al. |
| 2011/0040305 A1 | 2/2011 | Gomez et al. |
| 2011/0071675 A1 | 3/2011 | Wells et al. |
| 2011/0196199 A1 | 8/2011 | Donhowe et al. |
| 2011/0290856 A1 | 12/2011 | Shelton, IV et al. |
| 2011/0313573 A1 | 12/2011 | Schreiber et al. |
| 2012/0059391 A1 | 3/2012 | Diolaiti et al. |
| 2012/0059392 A1 | 3/2012 | Diolaiti |
| 2012/0132450 A1 | 5/2012 | Timm et al. |
| 2012/0154564 A1 | 6/2012 | Hoffman et al. |
| 2013/0231680 A1 | 9/2013 | Diolaiti et al. |
| 2013/0245375 A1 | 9/2013 | Dimaio et al. |
| 2013/0289767 A1 | 10/2013 | Lim et al. |
| 2014/0051922 A1 | 2/2014 | Guthart et al. |
| 2014/0052150 A1 | 2/2014 | Taylor et al. |
| 2014/0055489 A1 | 2/2014 | Itkowitz et al. |
| 2014/0135792 A1 | 5/2014 | Larkin et al. |
| 2014/0222021 A1 | 8/2014 | Diolaiti et al. |
| 2014/0232824 A1 | 8/2014 | Dimaio et al. |
| 2015/0065793 A1 | 3/2015 | Diolaiti et al. |
| 2015/0150639 A1 | 6/2015 | Diolaiti et al. |
| 2015/0182287 A1 | 7/2015 | Guthart et al. |

FOREIGN PATENT DOCUMENTS

| | | |
|---|---|---|
| EP | 812662 A1 | 12/1997 |
| EP | 1125557 A2 | 8/2001 |
| EP | 0732082 B1 | 9/2002 |
| EP | 1310844 A1 | 5/2003 |
| EP | 1424173 A2 | 6/2004 |
| JP | S61230895 A | 10/1986 |
| JP | H01280449 A | 11/1989 |
| JP | H04231034 A | 8/1992 |
| JP | H07184923 A | 7/1995 |
| JP | H07265321 A | 10/1995 |
| JP | H0889506 A | 4/1996 |
| JP | H08107875 A | 4/1996 |
| JP | H08154321 A | 6/1996 |
| JP | H08215211 A | 8/1996 |
| JP | H08275958 A | 10/1996 |
| JP | H10146341 A | 6/1998 |
| JP | H11000309 A | 6/1999 |
| JP | 2000500679 A | 1/2000 |
| JP | 2000300579 A | 10/2000 |
| JP | 2001000448 A | 1/2001 |
| JP | 2001061850 A | 3/2001 |
| JP | 2001104333 A | 4/2001 |
| JP | 2001202531 A | 7/2001 |
| JP | 2001287183 A | 10/2001 |
| JP | 2002103258 A | 4/2002 |
| JP | 2002287613 A | 10/2002 |
| JP | 2003053684 A | 2/2003 |
| JP | 2003300444 A | 10/2003 |
| JP | 2003339725 A | 12/2003 |
| JP | 2004105638 A | 4/2004 |
| JP | 2004223128 A | 8/2004 |
| JP | 2005110878 A | 4/2005 |
| JP | 2005303327 A | 10/2005 |
| JP | 2005334650 A | 12/2005 |
| JP | 2007029232 A | 2/2007 |
| JP | 2007508913 A | 4/2007 |
| JP | 2007531553 A | 11/2007 |
| JP | 2009006410 A | 1/2009 |
| JP | 2009012106 A | 1/2009 |
| JP | 2009525097 A | 7/2009 |
| WO | WO-9501757 | 1/1995 |
| WO | WO-9507055 A1 | 3/1995 |
| WO | H08299363 A | 11/1996 |
| WO | WO-9729690 | 8/1997 |
| WO | WO-9743942 A1 | 11/1997 |
| WO | WO-9743943 A1 | 11/1997 |
| WO | WO-2004014244 | 2/2004 |
| WO | WO-2005039391 A2 | 5/2005 |
| WO | WO-2005043319 A2 | 5/2005 |
| WO | WO-2006079108 A1 | 7/2006 |
| WO | WO-2007030173 A1 | 3/2007 |
| WO | WO-2007047782 A2 | 4/2007 |
| WO | WO-2007088206 A2 | 8/2007 |
| WO | WO-2007088208 A1 | 8/2007 |
| WO | WO-2007136768 A2 | 11/2007 |
| WO | WO-2007146987 A2 | 12/2007 |
| WO | WO-2008002830 A2 | 1/2008 |
| WO | WO-2008103383 A1 | 8/2008 |
| WO | WO-2009034477 | 3/2009 |

(56) References Cited

FOREIGN PATENT DOCUMENTS

| WO | WO-2009037576 | 3/2009 |
|---|---|---|
| WO | WO-2009158164 A1 | 12/2009 |
| WO | WO-2010039394 A1 | 4/2010 |

OTHER PUBLICATIONS

Askew, Scott R. et al., "Ground control testbed for space station freedom robot manipulators," IEEE Virtual Reality Annual International Symposium, 1993, pp. 69-75, IEEE.
Bajura, Michael et al., "Merging Virtual Objects with the Real World: Seeing Ultrasound Imagery within the Patient," Computer Graphics, Jul. 26, 1992, pp. 203-210, vol. 26, Issue 2, ACM Press.
Ben Gayed et al., "An Advanced Control Micromanipulator for Surgical Applications," Systems Science, 1987, pp. 123-134, vol. 13.
Cao, Caroline L., et al., "Task and motion analysis in endoscopic surgery," Submitted for Fifth Annual Symposium on Haptic Interfaces for Virtual Environment and Teloperator Systems for the Winter Meeting of ASME, 1996, pp. 1-32.
Christensen, B. et al., "Model based sensor directed remediation of underground storage tanks," International Conf. on Robotics and Automation, Sacramento, CA, Apr. 1991, pp. 1377-1383, vol. 2, IEEE.
Debus, Thomas et al., "Multichannel Vibrotacile Display for Sensory Substitution During Teleoperation," Proc. SPIE Telemanipulator and Telepresence Technologies VIII, 2001, pp. 42-49, vol. 4570, SPIE.
Dolan J.M. et al., "A Robot in an Operating Room: A Bull in a China Shop," 1987, pp. 1096-1097, vol. 2.
Elder, Matthew C. et al., "Specifying user interfaces for safety critical medical systems," Second Annual International Symposium on Medical Robotics and Computer Assisted Surgery, Nov. 1995, pp. 148-155.
Harris S.J. et al., "A robotic procedure for transurethral resection of the prostate," Second Annual International Symposium on Medical Robotics and Computer Assisted Surgery, 1995, pp. 264-271.
Hunter, Ian W. et al., "A teleoperated microsurgical robot and associated virtual environment for eye surgery," Presence: Teleoperators and Virtual Environments, 1993, pp. 265-280, vol. 2—No. 4, MIT Press.
Hunter, Ian W. et al., "Ophthalmic microsurgical robot and associated virtual environment," Comput. Biol. Med, 1995, vol. 25, Issue 2, pp. 173-182, Pergamon.
Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.
Jackson, Bernie G .et al., "Force Feedback and Medical Simulation," Interactive Technology and the New Paradigm for Healthcare, Morgan et al. (Eds ), 1995, pp. 147-151, vol. 24, IOS Press and Ohms.
Kazerooni, H., "Design and analysis of the statically balanced direct-drive robot manipulator," Robotics and Computer-Integrated Manufacturing, 1989, pp. 287-293, vol. 6, Issue 4.
Kilmer, R. D. et al., "Watchdog safety computer design and implementation," RI/SME Robots 8 Conference, Jun. 1984, pp. 101-117.
Kitagawa, Masaya et al., "Effect of Sensory Substitution on Suture Manipulation Forces for Surgical Teleoperation," 12th Annual Medicine Meets Virtual Reality Conference, 2005, 8 pages.
Kosugi, Yukio et al., "An articulated neurosurgical navigation system using MRI and CT Images," IEEE Transactions on Biomedical Engineering, 1988, pp. 147-152, vol. 35—Issue 2, IEEE.
Ng, W.S. et al., "Robotic Surgery, A First-Hand Experience in Transurethral Resection of the Prostate," IEEE Engineering in Medicine and Biology, Mar. 1993, pp. 120-125, vol. 12—Issue 1, IEEE.
Paul, Howard A. et al., "Development of a Surgical Robot for Cementless Total Hip Arthroplasty," Clinical Orthopaedics, Dec. 1992, pp. 57-66, vol. 285.
Preising, B. et al., "A Literature Review: Robots in Medicine," IEEE Engineering in Medicine and Biology, 1991, pp. 13-22, 71, vol. 10—Issue 2, IEEE.
Rosenberg, Louis B., "Human interface hardware for virtual laparoscopic surgery," Proceedings of the Interactive Technology and the New Paradigm for Healthcare, 1995, pp. 322-325, Amsterdam: IOS Press.
Schenker, Paul S. et al., "Development of a Telemanipulator for Dexterity Enhanced Microsurgery," 2nd Annual International Symposium on Medical Robotics and Computer Assisted Sugery, Nov. 4-7, Baltimore, Maryland, 1995, pp. 81-88.
Tavakoli, M., et al, A Force Reflective Master-Slave System for Minimally Invasive Surery, Proc. IEEE/RSJ International Conference on Intelligent Robots and Systems, 2003, pp. 3077-3082, vol. 4, IEEE.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Taylor, Russell H. et al., "Research Report: A Telerobotic Assistant for Laparoscopic Surgery," Accepted to IEEE EIMBS Magaine, Special Issue on "Robotics in Surgery," Dec. 1994, 24 pages.
Toon, John, "Virtual Reality for Eye Surgery," Georgia Tech Research news, 1993, 4 Pages.
Trivedi, Mohan M. et al., "Developing telerobotic systems using virtual reality concepts," 1993 IEEE/RSJ International Conference on Intelligent Robots and systems, 1993, pp. 352-359, vol. 1, IEEE.
Vertut, Jean and Phillipe Coiffet, *Robot Technology: Teleoperation and Robotics Evolution and Development*, English translation, Prentice-Hall, Inc., Inglewood Cliffs, NJ, USA 1986, vol. 3A, 332 pages.
Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.
Arai, Tatsuo et al., "Bilateral control for manipulators with different configurations," IECON Inn Conference on Industrial Electronics Control and Instrumentation, Oct. 22-26, 1984, pp. 40-45, vol. 1.
Baumann, Roger, "Haptic Interface for Virtual Reality Based Laparoscopic Surgery Training Environment," Theses No. 1734 Ecole Pholytechnique Federate de Lausanne, 1997, 104 Total Pages.
Bejczy, Antal K. et al., "Controlling Remote Manipulators through Kinesthetic Coupling," Computers in Mechanical Engineering, 1983, pp. 48-60, vol. 1-Issue 1.
Borovoi, A.V., "Stability of a manipulator with force feedback," Izv. AN SSSR Mekhanika Tverdogo Teal, 1990, pp. 37-45, vol. 25—Issue 1, Allerton Press, Inc.
Burdea, Grigore et al., "Dextrous Telerobotics with Force Feedback—an overview. Part 2: Control and Implementation," Robotica, 1991, pp. 291-298, vol. 9.
Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911-916.
Cohn, Michael C., "Medical Robotics," http://www-bsac.eecs.berkeley.edu/ , 1996, pp. 1-8 and 4.
Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.
Fisher, Scott S., "Virtual interface environment," IEEE/A1AA 7th Digital Avionics Systems Conference Ft. Worth Texas, 1986, pp. 346-350, IEEE.
Fu, K.S. et al., "Robotics: control, sensing, vision, and intelligence," 1987, pp. 12-76 and 201-265, Ch. 2 & 5, McGraw-Hill Book Company.
Fukuda, Toshio et al., "A new method of master-slave type of teleoperation for a micro-manipulator system," IEEE Microrobots and Teleoperations Workshop, 1987, 5 pages, IEEE.
Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.
Furuta, Katsuhisa et al., "Master slave manipulator based on virtual internal model following control concept," IEEE Intl. Conference on Robotics and Automation, 1987, pp. 567-572, vol. 1, IEEE.

(56) References Cited

OTHER PUBLICATIONS

Green, Philip, S. et al., "Mobile telepresence surgery," 2nd Annual Intl Symposium on Med. Robotics and Computer Assisted Surgery, Maryland Nov. 1995, pp. 97-103.
Hannaford, Blake et al., "Experimental and simulation studies of hard contact in force reflecting teleoperation," IEEE International Conference on Robotics and Automation Proceedings, 1988, pp. 584-589, vol. 1, IEEE.
Hill, John W., "Telepresence surgery demonstration system," Robotics and Automation, 1994, pp. 2302-2307, vol. 3, SRI International.
Inoue, Masao; "Six-Axis bilateral control of an articulated slave manipulator using a Cartesian master manipulator," Advanced robotics, 1990, pp. 139-150, vol. 4—Issue 2, Robotic society of Japan.
International Preliminary Examination Report for Application No. PCT/US00/08526, mailed on Jun. 29, 2001, 4 pages.
International Search Report for application No. PCT/US00/08526, Mailed on Jul. 14, 2000, 2 pages.
International Search Report for application No. PCT/US99/29145, Mailed on May 15, 2000, 1 page.
Jones, Daniel B. et al., "Next generation 3D videosystems may improve laprascopic task performance," Interactive Technology and the New Paradigm for Healthcare, 1995, pp. 152-160, Ch 25.
Kazerooni, H. et al., "The Dynamics and Control of a Haptic Interface Device," IEEE Transactions on Robotics and Automation, 1994, pp. 453-464, vol. 10—Issue 4, IEEE.
Kazerooni, H., "Human/Robot Interaction via the Transfer of Power and Information Signals Part I: Dynamics and Control Analysis," IEEE International Conference on Robotics and Automation, 1989, pp. 1632-1640, IEEE.
Kim, Won S. et al., "Active compliance and damping in telemanipulator control," Jet Propulsion Laboratory New technology Report, 1991, pp. 1-14a, vol. 15—Issue 4, JPL & NASA Case No. NPO-1796917466, Item 40.
Komada, Satoshi et al., "Bilateral robot hand based on estimated force feedback," IEEE Proceedings IECON 87 Cambridge MA, Nov. 3-6, 1987, pp. 602-607, vol. 2, IEEE.
Kwoh, Yik, San et al., "A Robot With Improved Absolute Positioning Accuracy for CT Guided Stereotactic Brain Surgery," IEEE Transactions on Biomedical Engineering, Feb. 1988, pp. 153-160, vol. 35—Issue 2, IEEE.
Lazarevic, Zoran, "Feasibility of a Stewart Platform with Fixed Actuators as a Platform for CABG Surgery Device," 1997, 45 pages, Master's Thesis Columbia University Department of Bioengineering.
Massie, Thomas H. et al., "The Phantom Haptic Interface: A Device for Probing Virtual Objects," Proceedings of the ASME Winter Annual Meeting, Symposium on Haptic Interfaces for Virtual Environment and Teleoperator Systems, 1994, 7 pages.
Mitsuishi, Mamoru et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.
Neisius B. et al., "Robotic manipulator for endoscopic handling of surgical effectors and cameras," 1st Intl. Symposium on Medical Robotics and Computer Assisted Surgery, 1994, pp. 169-176, vol. 2.
PCT/US07/71850 International Search Report and Written Opinion of the International Searching Authority, mailed Feb. 13, 2009, 9 pages.
PCT/US09/46234 International Search Report and Written Opinion of the International Searching Authority, mailed Sep. 9, 2009, 13 pages.
PCT/US09/56078 International Search Report and Written Opinion of the International Searching Authority, mailed Jan. 20, 2010, 12 pages.
PCT/US10/28886 International Search Report and Written Opinion of the International Searching Authority, mailed Jul. 6, 2010, 11 pages.

PCT/US10/28897 International Search Report and Written Opinion of the International Searching Authority, mailed Jul. 19, 2010, 16 pages.
PCT/US10/38246 International Search Report and Written Opinion of the International Searching Authority, mailed Sep. 14, 2010, 17 pages.
PCT/US2011/036109 International Search Report and Written Opinion of the International Searching Authority, mailed Oct. 19, 2011, 16 pages.
PCT/US2011/036109 Invitation to Pay Additional Fees and Partial International Search Report, mailed Aug. 18, 2011, 5 pages.
Sastry, Shankar et al., "Millirobotics for remote minamally invasive surgery," Proceedings of the Intl. Workshop on Some Critical Issues in Robotics, Singapore, Oct. 2-3, 1995, pp. 81-98.
Sastry, Shankar, http://robotics.eecs.berkeley.edu, Nov. 1, 1995, Total 8 pages.
Sastry, Shankar, "MilliRobotics in Minimally Invasive Telesurgery," Internet, http://robotics.eecs.berkeley.edu, 1996, 8 pages.
Supplementary European Search Report for Application No. EP00919930, mailed on May 9, 2003, 7 pages.
Supplementary Partial European Search Report for Application No. EP99966064, mailed on Jun. 12, 2007, 3 pages.
Taubes, Gary et al., "Surgery in Cyberspace," Discover magazine, Dec. 1994, vol. 15, issue 12, pp. 85-92.
Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited, Chapter 5,7,8,9.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Vibet, C., "Properties of Master Slave Robots," Motor-con, 1987, pp. 309-316.
Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.
Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.
Office Action mailed May 1, 2012 for Japanese Application No. 20090518470 filed Jun. 22, 2007, 7 pages.
Office Action mailed Sep. 3, 2014 for Japanese Application No. JP20120503535 filed Mar. 26, 2010.
Office Action mailed Jan. 26, 2015 for Japanese Application No. 20130186992 filed Sep. 10, 2013, 9 pages.
Zhang, Lunwei et al., "FBG Sensor Devices for Spatial Shape Detection of Intelligent Colonoscope," IEEE International Conference on Robotics and Automation, Apr. 2004, New Orleans, Louisiana, pp. 835-840.
Pose—definition from Merriam Webster Dictionary, 4 pages, [online], [retrieved on Apr. 3, 2015]. Retrieved from the Internet: <URL; http://www.merriam-webster.com/dictonary/pose>.
Posture—definition from Merriam Webster Dictionary, 4 pages, [online], [retrieved on Apr. 3, 2015]. Retrieved from the Internet: <URL; http://www.merriam-webster.com/dictonary/posture>.
3D Slicer web site,http//www.slicer.org,2003.
Abolmaesumi, Purang et al., "A User Interface for Robot-Assisted Diagnostic Ultrasound," IEEE Robotics and Automation Conference, 2001, pp. 1549-1554, vol. 2, IEEE.
Abolmaesumi, Purang et al., "Image Guided Control of a Robot for Medical Ultrasound," IEEE Transactions on Robotics and Automation, 2002, pp. 11-23, vol. 18—Issue 1, IEEE.
Ahlering, Thomas. E. et al., "Robotic radical prostatectomy: a technique to reduce pT2 positive margins," Urology, 2004, pp. 1224-1228, vol. 64 Issue 6, Elsevier Inc.
Arun, K.S. et al., "Least-Squares Fitting of Two 3-D Point Sets," IEEE Transactions on Pattern Analysis and Machine Intelligence (PAMI), vol. 9, No. 5, pp. 698-700, Sep. 1987.
Azuma, Ronald T., "A Survey of Augmented Reality," Teleoperators and Virtual Environments, 1997, pp. 355-385, vol. 6—No. 4.

(56) References Cited

OTHER PUBLICATIONS

Banovac, Filip et al., "Liver Tumor Biopsy in a Respiring Phantom with the Assistance of a Novel Electromagnetic Navigation Device," 2002, pp. 200-207, Springer-Verlag.
Bartels, Richard H. et al., "An Introduction to Splines for use in Computer Graphics and Geometric Modeling," 1987, 6 Pages total , Morgan kaufmann publishers, INC.
Bartels, Richard H. et al., "Solution of the Matrix Equation AX+XB=C," Communications of the ACM, 1972, pp. 820-826, vol. 15—Issue 9, ACM Press.
Berkelman, Peter J. et al., "A Compact Compliant Laparoscopic Endoscope Manipulator," IEEE International Conference on Robotics and Automation, 2002, pp. 1870-1875, vol. 2, IEEE.
Berkelman, Peter J. et al., "A miniature Instrument Tip Force Sensor for Robot/Human Cooperative Micro surgical Manipulation with Enhanced Force Feedback," Proceedings of the Third International Conference on Medical Image Computing and Computer-Assisted Intervention, Springer-Verlag, 2000, pp. 897-906, vol. 1935.
Berkelman, Peter J. et al., "A miniature microsurgical instrument tip force sensor for enhanced force feedback during robot-assisted manipulation," IEEE Transactions on Robotics and Automation, 2000, pp. 917-921, vol. 19—Issue 5, IEEE.
Berkelman, Peter J. et al., "Performance Evaluation of a Cooperative Manipulation Microsurgical Assistant Robot Applied to Stapedotomy," Medical Image Computing and Computer-Assisted Interventions, Lecture Notes in Computer Science, 2001, pp. 1426-1429, vol. 2208.
Besl, Paul J. et al., "A Method for Registration of 3-D Shapes," IEEE Transactions on Pattern Analysis and Machine Intelligence (PAM), vol. 14, Issue 2, pp. 239-256, Feb. 1992.
Bettini , A. et al., "Vision Assisted Control for Manipulation Using Virtual Fixtures: Experiments at Macro and Micro Scales," IEEE Conference on Robots and Automation (ICRA '02), May 11-15, 2002, pp. 3354-3361, vol. 4, IEEE.
Bettini , A. et al., "Vision Assisted Control for Manipulation Using Virtual Fixtures," IEEE/RSJ International Conference on Intelligent Robots and Systems (IROS), Oct. 29-Nov. 3, 2001, pp. 1171-1176, vol. 2.
Bettini, Alessandro et al., "Vision Assisted Control for Manipulation Using Virtual Fixtures," IEEE Transactions on Robotics, 2004, pp. 953-966, vol. 20—Issue 6, IEEE.
Birkett, Desmond H., "Three-Dimensional Video Imaging Systems," Chapter 1 in Primer of Robotic & Telerobotic Surgery, Eds. Garth H. Ballantyne et al., Pub. By Lippincott Williams & Wilkins, Philadelphia, 2004, pp. 7-11.
Boctor, Emad et al., "A Novel Closed Form Solution for Ultrasound Calibration," IEEE International Symposium on Biomedical Imaging (ISBI), Arlington, VA, vol. 1, pp. 527-530, Apr. 15-18, 2004.
Boctor, Emad, M. et al., "A dual-armed robotic system for intraoperative ultrasound guided hepatic ablative therapy: a prospective study," Proc of IEEE 2004 International Conference on Robotics & Automation, 2004, pp. 2517-2522, vol. 3, IEEE.
Boctor, Emad, M. et al., "A Rapid calibration method for registration and 3D tracking of ultrasound images using spatial localizer," Ultrasonic Imaging and Signal Processing, 2003, pp. 521-532, vol. 5035, SPIE.
Boctor, Emad, M. et al., "CISUS: An integrated 3D ultrasound system for IGT using a modular tracking API," Proceedings of the SPIE, 2004, pp. 247-256, vol. 5367, SPIE.
Boctor, Emad, M. et al., "Development of a Robotically-Assisted 3-D Ultrasound System for Radiofrequency Ablation of Liver Tumors," 6th World Congress of the Hepato-Pancreato-Biliary Association, Abstract No. 167, 2004, pp. 46, vol. 6-Supplement 1, Taylor & Francis Health Science.
Boctor, Emad, M. et al., "PC Based system for calibration, Reconstruction Processing and Visualization of 3D Ultrasound Data Based on a Magnetic-Field Position and Orientation Sensing System," Proceedings of the International Conference on Computational Science—Part II, Lecture Notes in Computer Science , 2001, pp. 13-22, vol. 2074, Springer.
Boctor, Emad, M. et al., "Robot-assisted 3D strain imaging for monitoring thermal ablation of liver," Annual congress of the Society of American Gastrointestinal Endoscopic Surgeons (SAGES), Emerging Technology Lunch Poster TP004, 2005, pp. 240-241.
Boctor, Emad, M. et al., "Robotic Strain Imaging for Monitoring Thermal Ablation of Liver," Medical Image Computing and Computer-Assisted Intervention MICCAI, 2004, pp. 81-88, vol. 2, Springer-Verlag.
Boctor, Emad, M. et al., "Robotically assisted intraoperative ultrasound with application to ablative therapy of liver cancer," Medical Imaging:Visualization, Image Guided Procedures, and Display, 2003, pp. 281-291, vol. 5029, SPIE.
Boctor, Emad, M. et al., "Tracked 3D ultrasound in radio-frequency liver ablation," in Medical Imaging 2003:Ultrasonic Imaging and Signal Processing, 2003, pp. 174-182, vol. 5035, SPIE.
Boudet,Sylvie et al., "An Integrated Robotics and Medical Control Device to Quantify Atheromatous Plaques: Experiments on the Arteries of a Patient," Proc of IEE/RSH International Conference on Intelligent Robots and Systems, 1997, pp. 1533-1538, vol. 3.
Brown, Myron M. et al., "Advances in Computational Stereo," IEEE Transactions on Pattern Analysis and Machine Intelligence (PAMI), 2003, pp. 993-1008, vol. 25 Issue, IEEE.
Burschka, Darius et al., "Scale-Invariant Registration of Monocular Endoscopic Images to CT-Scans for Sinus Surgery," Med Image Anal, 2004, pp. 413-421, vol. 2, Springer-Verlag.
Burschka, Darius et al., "Scale-Invariant Registration of Monocular Stereo Images to 3D Surface Models," IEEE Int. Conf. on Robots and Systems, 2004, pp. 2581-2586, vol. 3, IEEE.
Burschka, Darius et al., "Navigating Inner Space: 3-D Assistance for Minimally Invasive Surgery," Robotics and Autonomous Systems, 2005, pp. 5-26, vol. 52—Issue 1, Elsevier.
Burschka, Darius et al., "Principle and Practice of Real-Time Visual Tracking for Navigation and Mapping," IEEE Workshop on Robotic Sensing: Robotics in the Automotive Industry, 2004, pp. 1-8, IEEE.
Bzostek, Andrew, "Computer-Integrated needle therapy systems: Implementation and Analysis," Computer Science, 2005, 379 pages.
Bzostek, Andrew et al., "A Testbed System for Robotically Assisted Percutaneous Pattern Therapy," Medical Image Computing and Computer-Assisted Surgery, Lecture Notes in Computer Science, 1999, pp. 1098-1107, vol. 1679, Springer.
Bzostek, Andrew et al., "An automated system for precise percutaneous access of the renal collecting system," Proceedings of the First Joint Conference on Computer Vision, Virtual Reality and Robotics in Medicine and Medial Robotics and Computer-Assisted Surgery, Lecture Notes in Computer Science, 1997, pp. 299-308, vol. 1205, Springer-Verlag.
Bzostek, Andrew, "Image Guided Percutaneous Pattern Placement in Soft Tissue," The Johns Hopkins University Dept. of Computer Science: Baltimore, 1997, pp. 2007-01-2007-22.
Cadeddu, Jeffrey A. et al., "A Robotic System for Percutaneous Renal Access," The Journal of Urology, 1997, pp. 1589-1593, vol. 158—Issue 4.
Cadeddu, Jeffrey et al., "A robotic system for percutaneous renal access incorporating a remote center of motion design," Journal of Endourolog, 1998, S237, vol. 12.
Cannon, Jeremy W. et al., "Real-time three-dimensional ultrasound for guiding surgical tasks," Computer Aided Surgery, 2003, pp. 82-90, vol. 8—No. 2, John Wiley & Sons.
Carr, J., "Surface reconstruction in 3D medical imaging," PhD Thesis, University of Canterbury, Christchurch, New Zealand, 1996, 223 Pages.
Cash, David M. et al., "Incorporation of a laser range scanner into an image-guided surgical system," The International Society for Optical Engineering (SPIE), Medical Imaging 2003: Visualization, Image-Guided Procedures, and Display; San Diego, CA, Ed. Robert L. Galloway, 2003, pp. 269-280, vol. 5029.
Chang, Jun Keun et al., "Intravascular micro active catheter for minimal invasive surgery," 1st Annual International Conference on Microtechnologies in Medicine and Biology, 2000, pp. 243-246.
Chen, Homer H. "A Screw Motion Approach to Uniqueness Analysis of Head-Eye Geometry," Computer Vision and Pattern Recognition, 1991, pp. 145-151, IEEE.

(56) References Cited

OTHER PUBLICATIONS

Chinzei, Kiyoyuki et al., "MR Compatible Surgical Assist Robot: System Integration and Preliminary Feasibility Study," in Proceedings of Third International Conference on Medical Imaging and Computer Assisted Surgery (MICCAI), 2000, pp. 921-930, vol. 1935, Springer-Verlag.
Choti, Michael A. et al., "Trends in Long Term Survival Following Liver Resection for Hepatic Colorectal Metastases," Ana Surg, 2002, pp. 759-766, vol. 235—No. 6, Lippincott Williams & Wilkins.
Choti, Michael A., "Hepatic Radiofrequency Ablation," Cancer Journal, 2000, pp. S291-S292, vol. 6—issue 4, Jones and Bartlett.
Choti, Michael A., "Surgical Management of Hepatocellular Carcinoma: Resection and Ablation," Journal of Vascular and Interventional Radiology, 2002, pp. S197-S203, vol. 13—No. 9.
Chung, Mathew et al., "Laparascopic Radiofrequency Ablation of Unresectable Hepatic Malignancies," Surg Endosc, 2001, pp. 1020-1026, vol. 15—No. 9, Springer-Verlag.
Cleary,K. et al., "Robotically-assisted spine nerve blocks," Radiology, 2001, 1 page, vol. 221—No. 618.
D'Angelica M., "Staging Laparoscopy for Potentially Respectable Noncolorectal," Ann Surg Oncol, 2002, pp. 204-209, vol. 9—No. 2, Lippincott Williams & Wilkins.
Daniilidis, Konstantinos, Hand-Eye Calibration Using Dual Quaternions, Int. J. of Robotics Research, 2000, pp. 286-298, vol. 19—No. 3, Sage Publications, Inc.
Davies, Brain L. et al., "A Robotic system for tkr surgery," Proceedings of 3rd Annual North American Program on Computer Assisted Orthopaedic Surgery (CAOS USA), University of Pittsburgh Medical Center, Pittsburgh, Pennsylvania,published in Computer Aided Surgery, Jun. 17-19, 1999, p. 339, vol. 4—Iss. 6.
Davies, S. C.et al., "Ultrasound quantitaion of respiratory organ motion in the upper abdomen," British Journal of Radiology, 1994, pp. 1096-1102, vol. 37—Iss. 803.
De Cunha, D. et al., The MIDSTEP System for Ultrasound guided Remote Telesurgery, Proceedings of the 20th Annual International Conference of the IEEE Engineering in Medicine and Biology Society, 1998, pp. 1266-1269, vol. 3—No. 29, IEEE.
Degoulange, E. et al., "HIPPOCRATE: an intrinsically safe robot for medical applications," IEEE/RSH International Conference on Intelligent Biomedicine, 1998, pp. 959-964, vol. 2, IEEE.
Delgorge, Cecile et al., "A Tele-Operated Mobile Ultrasound Scanner Using a Light-Weight Robo," IEEE Transactions on Information Technology in Biomedicine, 2005, pp. 50-58, vol. 9 No. 1, IEEE.
Dewan, Maneesh et al., "Vision-Based Assistance for Ophthalmic Micro-Surgery," Proceedings of Seventh International Conference on Medical Image Computing and Computer-Assisted Intervention (MICCAI), 2004, pp. 49-57, vol. 2, Springer-Verlag.
Dodds, Zachary et al., "A hierarchical architecture for vision-based robotic manipulation tasks," in Proceedings of the International Conference on Vision Systems, 1999, pp. 312-330, vol. 542, Springer-Verlag.
Doggett, Stephen W., "Image Registered Real Time Intra-Operative Treatment Planning: Permanent Seed Brachytherapy," 2000, pp. 4.
Eldridge, B. et al., "A Remote Center of Motion Robotic Arm for Computer Assisted Surgery," Robotica, 1996, pp. 103-109, vol. 14 Issue 1.
Ellsmere, James et al., "A navigation system for augmenting laparoscopic ultrasound," Medical Image Computing and Computer-Assisted Intervention, Lecture Notes in Computer Science, 2003, pp. 184-191, Springer.
Fattal, Lischinsk, "Variational Classification for Visualization of 3D Ultrasound Data," Proceedings of the conference on Visualization, 2001, pp. 403-410, IEEE Computer Society.
Fenster, Aaron, et al., "3-D Ultrasound Imaging:A Review," IEEE Engineering and Medicine and Biology Magazine, Nov.-Dec. 1996, pp. 41-51, vol. 15—Issue 6, IEEE.
Fenster, Aaron, et al., "Three-dimensional ultrasound imaging of the prostate," SPIE International Symposium on Medical Imaging,San Diego, California,Published in SPIE: Medical Physics, Feb. 20-26, 1999, pp. 2-11, vol. 3859, SPIE.

Fichtinger, Gabor et al., "Robotically Assisted Percutaneous Local Therapy and Biopsy," 10th International Conference of Advance Robotics, 2001, pp. 133-151, IEEE.
Fichtinger, Gabor et al., "Transrectal prostate biopsy inside closed MRI scanner with remote actuation under real-time image guidance," Medical Image Computing and Computer-Assisted Intervention, Lecture Notes in Computer Science, 2002, pp. 91-98, vol. 2488, Springer Verlag.
Fichtinger, Gabor et al., "Surgical CAD/CAM and its application for robotically assisted percutaneous procedures," 30th Applied Imagery Pattern Recognition Workshop (AIPR), 2001, pp. 3-8, IEEE.
Fichtinger, Gabor et al., "System for Robotically Assisted Prostate Biopsy and Therapy With intraOperative CT Guidance," Journal of Academic Radiology, 2002, pp. 60-74, vol. 9 No. 1, Elsevier.
Frantz D.D et al., "Accuracy assessment protocols for electromagnetic tracking systems," Physics in Medicine and Biology, 2003, pp. 2241-2251, Issue 48.
Fuchs, Henry et al., "Augmented Reality Visualization for Laparoscopic Surgery," Medical Image Computing and Computer-Assisted Intervention, 1998, pp. 934-943, vol. 1496, Springer-Verlag.
Funda, Janez, "An experimental user interface for an interactive surgical robot," In 1st International Symposium on Medical Robotics and Computer Assisted Surgery (MRCAS 94), Pittsburgh, 1994, pp. 196-201, 203.
Funda, Janez et al., "Comparison of two manipulator designs for laparoscopic surgery," SPIE International Symposium on Optical Tools for Manufacturing and Advanced Automation, 1994, pp. 172-183, vol. 2351, Telemanipulator and Telepresence Technologies.
Funda, Janez et al., "Control and evaluation of a 7-axis surgical robot for laparoscopy," IEEE Int. Conf. on Robotics and Automation, 1995, pp. 1477-1484, vol. 2, IEEE.
Funda, Janez et al., "Image-Guided Command and Control of a Surgical Robot," Proc. Medicine Meets Virtual Reality II, 1994, pp. 52-57.
Funda, Janez et al., "Optimal Motion Control for Teleoperated Surgical Robots," Intl. Symp. on Optical Tools for Manuf. & Adv Autom,Telemanipulator Technology and Space Telerobotics, 1993, pp. 211-222, vol. 2057, SPIE.
Garrett, William F. et al., "Real-Time Incremental Visualization of Dynamic Ultrasound Volumes Using Parallel BSP Trees," IEEE Proceedings Visualization, 1996, pp. 235-240, 490, IEEE.
Gee, Andrew et al., "Processing and visualizing three-dimensional ultrasound data," Journal of Radiology, 2004, pp. 186-193, vol .77.
Gelb, Arthur et al., "Applied Optimal Estimation," 1974, 4 Pages Total.
Gennari, G. et al., "Probabilistic data association methods in visual tracking of groups," IEEE Conference on Computer Vision and Pattern Recognition, 2004, pp. I-790-1-797, vol. 1—issue. 27, IEEE.
Gigot, Jean-Francois et al., "Laparoscopic Liver Resection for Malignant Liver Tumors Prclimary Results of a Multicenter European Study," Ann Surg, 2002, pp. 90-97, vol. 236—issue 1.
Gonzales, Adriana Vilchis et al., "A System for Robotic Tele-echography," Medical Image Computing and Computer-Assisted Intervention, 2001, pp. 326-334, vol. 2208, Springer.
Grimson, W. Eric et al., "Automated Registration for Enhanced Reality Visualization in Surgery," 1st International Symposium on Medical Robotic and Computer Assisted Surgery (MRCAS), Pittsburgh, 1994, pp. 82-89.
Grimson, W.E.L., et al., "An automatic registration method for frameless stereotaxy, image guided surgery, and enhanced reality visualization," IEEE Transactions on Medical Imaging, vol. 15, No. 2, Apr. 1996, pp. 129-140.
Hager, Gregory D., "A Modular System for Robust Hand Eye Coordination Using Feedback from Stereo Vision," IEEE Transactions on Robotics and Automation, 1997, pp. 582-595, vol. 13—issue(4), IEEE.
Hager, Gregory D. et al., "Efficient Region Tracking With Parametric Models of Geometry and Illumination," IEEE Transactions on Pattern Analysis and Machine Intelligence, 1998, pp. 1025-1039, vol. 20—issue. 10, IEEE.

(56) References Cited

OTHER PUBLICATIONS

Hager Gregory D. et al., "Multiple Kernel Tracking with SSD," Proceedings of the IEEE Conference on Computer Vision and Pattern Recognition (CVPR 2004), 2004, pp. I-790-I-797, vol. 1—issue 27, IEEE.

Hager, Gregory D. et al., "The XVision System: A Portable Substrate for Real Time Vision Applications," 1998, pp. 23-37, vol. 69—issue 1.

Hannaford, Blake et al., "Performance Evaluation of a Six-Axis Generalized Force-Reflecting Teleoperator," IEEE Transactions on Systems, Man, and Cybernetics, 1991, pp. 620-633, vol. 21—No. 3, IEEE.

Harris, S.J. et al., "Experiences with Robotic Systems for Knee Surgery," First Joint Conference of CVRMed and MRCAS. Mar. 19-22, 1997, Grenoble, France; Springer, 1997, pp. 757-766,.

Herline, Alan J. et al., "Image-Guided Surgery: Preliminary Feasibility Studies of Frameless Stereotactic Liver Surgery," Archives of Surgery, 1999, pp. 644-650, vol. 134—No. 6.

Herline, Alan J. et al., "Surface Registration for Use in Interactive," Image-Guided Liver Surgery, Computer Aided Surgery, 2000, pp. 11-17, vol. 5—No. 2.

Herman, Barry C., et al, "Telerobotic surgery creates opportunity for augmented reality surgery," Abstract No. T1F2, Telemedicine Journal and E-Health, vol. 11, Issue 2, p. 203, Apr. 2005.

Herman, Barry C., "On the Role of Three Dimensional Visualization for Surgical Applications in Interactive Human Machine Systems," Masters of Science Thesis in Computer Science, The Johns Hopkins University, Baltimore, 2005, 216 pages.

Hespanha J.P. et al., "What Tasks Can Be Performed with an Uncalibrated Stereo Vision System", International Journal of Computer Vision, 1999, pp. 65-85, vol. 35—issue. (1).

Ho, S. C.et al., "Robot Assisted Knee Surgery," IEEE Engineering in Medicine and Biology Magazine, 1995, pp. 292-300, vol. 14—Iss. 3, IEEE.

Hong, Jae-Sung et al., "A Motion Adaptable Needle Placement Instrument Based on Tumor Specific Ultrasonic Image Segmentation," Fifth International Conference on Medical Image Computing and Computer Assisted Intervention, MICCAI '02, Tokyo, Japan, Jul. 2002, pp. 122-129.

Horn, Berthold K.P., "Closed-form solution of absolute orientation using unit quaternions," Journal of the Optical Society of America A, vol. 4, No. 4, pp. 629-642, Apr. 1987.

Hutchinson, Seth et al., "A Tutorial Visual Servo Control," IEEE Transactions on Robotics and Automation, 1996, pp. 651-670, vol. 12 issue.5, IEEE.

IEEE Systems and Software Engineering—Recommended Practice for Architectural Description of Software-Intensive Systems, IEEE Std 1471-2000, 34 pages, First Edition, Jul. 15, 2007.

Intuitive Surgical, Inc., "Intuitive Surgical daVinci API v5.0 Reference Manual," generated Jul. 17, 2006, 149 pages.

Jain, Ameet Kumar et al., "Understanding Bone Responses in B-mode Ultrasound Images and Automatic Bone Surface Extraction using a BayesianProbabilistic Framework," SPIE Medical Imaging, 2004, pp. 131-142, vol. 5373.

Johns Hopkins University and Intuitive Surgical, Inc., "System Requirements for the Surgical Assistant Workstation," Rev. 2, Jan. 29, 2007, 17 pages.

Joskowicz, Leo et al., "Computers in Imaging and Guided Surgery," Computing in Science and Engineering, 2001, pp. 65-72, vol. 3—Issue: 5, IEEE.

Jurie, Frederic et al., "Hyperplane Approximation for Template Matching," IEEE Transactions on Pattern Analysis and Machine Intelligence(PAMI), 2002, pp. 996-1000, vol. 24—Issue 7, IEEE.

Kane, Robert A., "Intraoperative Ultrasonography, History, Current State of the Art, and Future Directions," J Ultrasound Med, 2004, pp. 1407-1420, vol. 23.

Kaplan, Irving, "Minimizing Rectal and Urinary Complications in Prostate Brachytherapy," Journal of Endourology, 2000, pp. 381-383.

Kapoor, Ankur and Russell H. Taylor, "A constrained optimization approach to virtual fixtures for multi-handed tasks," 2008 International Conference on Robotics and Automation (ICRA 2008), May 19-23, 2008, Pasadena, California, pp. 3401-3406.

Kapoor, Ankur et al., "Constrained Control for Surgical Assistant Robots," 2006 IEEE International Conference on Robotics and Automation (ICRA 2006), Orlando, Florida, May 15-19, 2006, pp. 231-236.

Kapoor, Ankur et al., "Simple Biomanipulation Tasks with a Steady Hand Cooperative Manipulator," In Proceedings of the Sixth International Conference on Medical Image Computing and Computer Assisted Intervention—MICCAI Lecture Notes in Computer Science, 2003, vol. 1, Springer.

Kapoor, Ankur et al., "Suturing in Confined Spaces: Constrained Motion Control of a Hybrid 8-DOF Robot," Proceedings, 12th International Conference on Advanced Robotics, 2005, pp. 452-459.

Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.

Kavoussi, Louis R., "Laparoscopic donor nephrectomy," Kidney International, 2000, pp. 2175-2186, vol. 57.

Kazanzides, Peter et al., "A cooperatively-controlled image guided robot system for skull base surgery," Medicine Meets Virtual Reality 16 (MMVR 16) Conference, Jan. 30-Feb. 1, 2008, Long Beach, California, J.D. Westwood et al., eds., IOS Press, 2008, pp. 198-203.

Kazanzides, Peter et al., "Force Sensing and Control for a Surgical Robot," Int. Conference on Robotics and Automation, May 1992, Nice, France; pp. 612-617, vol. 1, IEEE.

Kazerooni, H., "Human Extenders," ASME J. Dynamic Systems, Measurements and Control, 1993, pp. 281-290, vol. 115 No. 2(B).

Koizumi, Naoshi et al., "Development of Three-Dimensional Endoscopic Ultrasound System with Optical Tracking," Medical Image Computing and Computer-Assisted Intervention—MCCAI '02, Tokyo, 2002, pp. 60-65, vol. 2488, Springer-Verlag.

Koizumi, Norihiro et al., "Continuous Path Controller of Slave Manipulator in Remote Ultrasound Diagnostic System," Int. Conference on Robotics and Automation (ICRA 2002), 2002, pp. 3368-3373, vol. 4, IEEE.

Kon, Ryan et al., "An open-source ultrasound calibration toolkit," Medical Imaging Ultrasonic Imaging and Signal Processing, 2005, pp. 516-523, vol. 5750, SPIE.

Korein James U. et al., "A Configurable System for Automation Programming and Control," IEEE Conf. on Robotics and Automation. San Francisco, 1986, pp. 1871-1877, vol. 3, IEEE.

Kragic D. et al., "Human-Machine Collaborative Systems for Microsurgical Applications," International Symposium on Robotics Research, 2005, pp. 731-741, vol. 24—Issue 9, Sage Publications.

Kruchten, Philippe B., "The 4+1 View Model of Architecture," IEEE Software, vol. 12, Issue 6, pp. 42-50, Nov. 1995.

Krupa, A. et al., "Automatic 3-D Positioning of Surgical Instruments during Laparoscopic Surgery Using Automatic Visual Feedback," Proceedings of the 5th International Conference on Medical Image Computing and Computer-Assisted Intervention—Part , Lecture Notes in Computer Science, 2002, pp. 9-16, vol. 2488, Springer Verlag.

Kumar, Rajesh, "An Augmented Steady Hand System for Precise Micromanipulation," 2001, 109 pages.

Kumar, Rajesh et al., "An Augmentation System for Fine Manipulation," Proceedings of the Third International Conference on Medical Image Computing and Computer-Assisted Intervention, Lecture Notes in Computer Science, 2000, pp. 956-964, vol. 1935, Springer Verlang.

Kumar, Rajesh et al., "Application of Task-Level Augmentation for Cooperative Fine Manipulation Tasks in Surgery," Proceedings of the 4th International Conference on Medical Image Computing and Computer-Assisted Intervention, Lecture Notes in Computer Science, 2001, pp. 1417-1418, vol. 2208, Springer Verlang.

Kumar, Rajesh et al., "Experiments with a Steady Hand Robot in Constrained Compliant Motion and Path Following", 1999, pp. 92-97, IEEE.

Kumar, Rajesh et al., "Preliminary Experiments in Cooperative Human/Robot Force Control for Robot Assisted Microsurgical Manipulation," Conference on Robotics and Automation, 2000, pp. 610-617, vol. 1, IEEE.

(56) References Cited

OTHER PUBLICATIONS

Kumar, Rajesh et al., "Preliminary experiments in robot/human microinjection," IEEE/RSJ International Conference on Intelligent Robots and Systems, 2003, pp. 3186-3191, vol. 3, IEEE.

Lacroute, Philippe et al., "The VolPack Volume Rendering Library," 2003, pp. 4.

Lacroute, Philippe G., "Fast Volume Rendering Using a Shear-Warp Factorization of the Viewing Transformation PhD Thesis," Computer Science, Stanford, California, 1995, 236 Pages.

Lang, Samuel J., Xvision 2—A Framework for Dynamic Vision. Masters Thesis, Computer Science, Johns Hopkins University, Baltimore, 2001, pp. 1-49.

Lange, Thomas et al., Augmenting Intraoperative 3D Ultrasound with Preoperative Models for Navigation in Liver Surgery, Medical Image Computing and Computer-Assisted Interventions, 2004, pp. 534-541, vol. 3217, Springer Verlag.

Lau, William W. et al., "Stereo-Based Endoscopic Tracking of Cardiac Surface Deformation," Proceedings of Seventh International Conference on Medical Image Computing and Computer-Assisted Intervention (MICCAI), Lecture Notes in Computer Science, 2004, pp. 494-501, vol. 2, Springer Verlag.

Lavonius, Maija I. et al., "Staging of Gastric Cancer: A Study with Spiral Computed Tomography,Ultrasonography, Laparoscopy, and Laparoscopic Ultrasonography," Surgical Laparoscopy, Endoscopy & Percutaneous Techniques, 2002, pp. 77-81, vol. 12—No. 2, Lippincott Williams & Wilkins, Inc.

Lawson, Charles L. et al., "Linear least squares with linear inequality constraints Solving Least Squares Problems," 1974, pp. 158-173, Prentice Hall Inc.

Lee Jr, Fred T. et al., "CT-monitored percutaneous cryoablation in a pig liver model," Radiology, 1999, pp. 687-692, vol. 211(3).

Leven, Joshua, "A Telerobotic Surgical System With Integrated Robot-Assisted Laparoscopic Ultrasound Capability," Thesis for Master of Science in Engineering in Computer Science, The Johns Hopkins University, Baltimore, Maryland, May 2005, 63 pages.

Leven, Joshua et al. "DaVinci Canvas: A Telerobotic Surgical System with Integrated, Robot-Assisted, Laparoscopic Ultrasound Capability," Medical Image Computing and Computer-Assisted Intervention (MICCAI), Lecture Notes in Computer Science, J. Duncan et al. Eds., Palm Spring, Springer Verlag, 2005, vol. 3749, pp. 811-818.

Levoy, Marc, "Display of Surfaces from Volume Data," IEEE Computer Graphics and Applications, 1988, pp. 29-37, vol. 8—Iss. 3, IEEE.

Li, Ming and Russell H. Taylor, "Spatial Motion Constraints in Medical Robots Using Virtual Fixtures Generated by Anatomy," IEEE International Conference on Robotics and Automation, New Orleans, Apr. 2004, pp. 1270-1275.

Li, Ming and Russell H. Taylor, "Performance of surgical robots with automatically generated spatial virtual fixtures," IEEE International Conference on Robotics and Automation, Barcelona, Spain, Apr. 2005, pp. 217-222.

Li, Ming et al, "A Constrained Optimization Approach to Virtual Fixtures," IEEE/RSJ International Conference on Intelligent Robots and Systems (IROS 2005), Edmonton, Alberta, Canada, Aug. 2-6, 2005, pp. 1408-1413.

Li, Ming et al., "Optimal Robot Control for 3D Virtual Fixture inConstrained ENT Surgery," Proceedings of the Sixth International Conference on Medical Image Computing and Computer Assisted Intervention—MICCAI, Lecture Notes in Computer Science, 2003, pp. 165-172, vol. I, Springer Verlag.

Li, Ming et al., "Recognition of Operator Motions for Real-Time Assistance using Virtual Fixtures," IEEE, HAPTICS 2003, 11th Symposium on Haptic Interfaces for Virtual Environment and Teleoperator Systems, Mar. 22-23, 2003, pp. 125-131, IEEE.

Li, Ming, "Intelligent Robotic Surgical Assistance for Sinus Surgery," Ph.D. Dissertation, Computer Science, Johns Hopkins University, Baltimore, 2005, 229 pages.

Loser, Michael H. et al., "A New Robotic System for Visually Controlled Percutaneous Interventions under CT Fluoroscopy," Medical Image Computing and Computer-Assisted Interventions, Lecture Notes in Computer Science, 2000, pp. 887-896, vol. 1935, Springer Verlag.

Loser, Michael H. et al., "Visual servoing for automatic and uncalibrated percutaneous procedures," SPIE Medical Imaging, 2000, pp. 270-281, vol. 3976, SPIE.

Maehara, S. et al., "Laparoscopy-Assisted Hepatectomy Using the Endoclose," Surg Endosc, 2002, pp. 1362-1365, vol. 16(9), Springer Verlag.

Maier, Georg, E. et al., "A Dynamically Configurable General Purpose Automation Controller," Proceedings of IFAC/IFIP Symp. on Software for Computer Control, 1986, pp. 47-52, Pergamon Press.

Mala, T. et al., "A Comparative Study of the Short-Term Outcome Following Open and Laparoscopic Liver Resection of Colorectal Metastases," Surg Endosc, 2002, pp. 1059-1063, vol. 16(7), Springer Verlag.

Marayong, Panadda et al., "Spatial Motion Constraints: Theory and Demonstrations for Robot Guidance Using Virtual Fixtures," IEEE International Conference on Robotics and Automation Robotics and Automation, 2003, pp. 1954-1959, vol. 2, No. 14-19, IEEE. 1:1.

Marescaux, Jadques and Francesco Rubino, "Virtual Operative Fields for Surgical Simulation," Chapter 4 in Primer of Robotic & Telerobotic Surgery, Eds. Garth H. Ballantyne et al., Pub. By Lippincott Williams & Wilkins, Philadelphia, 2004, pp. 26-31.

Masamune K., et al., "Development of a MRI Compatible Needle Insertion Manipulator for Stereotactic Neurosurgery," Journal of Image Guided Surgery, 1995, vol. 1, pp. 242-248.

Masamune, Ken et al., "Development of a MRI Compatible Needle Insertion Manipulator for Stereotactic Neurosurgery," Image Guid Surg, 1995, pp. 165-172.

Masamune Ken et al., "Development of CT-PAKY frame system—CT image guided needle puncturing manipulator and a single slice registration for urological surgery," Proc. 8th annual meeting of Japanese Society for Computer Aided Surgery (JSCAS), 1999, pp. 89-90.

Masamune, Ken et al., "System for Robotically Assisted Percutaneous Procedures With Computed Tomography Guidance," Journal of Computer-Assisted Surgery, 2001, pp. 370-383, vol. 6—No. 6, Wiley-Liss, Inc.

Masamune, Ken H. et al., "A Newly Developed Stereotactic Robot with Detachable Drive for Neurosurgery," 1st International Conference on Medical Image Computing and Computer-Assisted Intervention—MICCAI,Cambridge, Massachusetts; Springer, Oct. 11-13, 1998, pp. 215-222, vol. 1496.

Mayer, Hermann et al., "Skill Transfer and Learning by Demonstration in a Realistic Scenario of Laparoscopic Surgery," International Conference on Humanoids, 2003, 17 pages, IEEE.

Mayer, Hermann et al., "The Endo [PA]R System for Minimally Invasive Robotic Surgery," IEEE/RSJ International Conference on Intelligent Robots and Systems (IROS), 2004, pp. 3637-3642, vol. 4, IEEE.

Megali, Giusepp et al., "A Computer-Assisted Robotic Ultrasound-Guided Biopsy System for Video-Assisted Surgery," Proceedings of the 4th International Conference on Medical Image Computing and Computer-Assisted Intervention, Lecture Notes in Computer Science, 2001, pp. 343-350, vol. 2208, Springer-Verlag.

Menack, M. et al., "Staging of pancreatic and ampullary cancers for resectability using laparoscopy with laparoscopic ultrasound," Surg Endosc, 2001, pp. 1129-1134, vol. 15—No. 10, Springer-Verlag.

Menon, Mani, "Vattikuti Institute prostatectomy, a technique of robotic radical prostatectomy for management of localized carcinoma of the prostate: experience of over 1100 cases," Urol Clin N Am, 2004, pp. 701-717, vol. 31.

Merola, Stephen et al., "Comparison of Laparoscopic Colectomy With and Without the Aid of a Robotic Camera Holder," Surg Laparosc Endosc Percutan Tech, 2002, pp. 45-61, vol. 12—No. 1, Lippincott Williams & Wilkins, Inc.

Migga, Michael I. et al., "Intraoperative Registration of the Liver for Image-Guided Surgery System," The International Society for Optical Engineering (SPIE), Medical Imaging 2003: Visualization, Image-Guided Procedures, and Display; San Diego, CA, Ed. Robert L. Galloway, 2003, pp. 350-359, vol. 5029.

(56) References Cited

OTHER PUBLICATIONS

Mitsuishi, Mamoru et al., "Remote Ultrasound Diagnostic System," Conf. on Robotics and Automation, 2001, pp. 1567-1574, vol. 2, IEEE.

Mourgues, Fabien et al., "Flexible Calibrations of Actuated Stereoscopic Endoscope for Overlay in Robot Assisted Surgery," Proceedings of the 5th International Conference on Medical Image Computing and Computer-Assisted Intervention—Part I, Lecture Notes in Computer Science, 2002, pp. 25-34, vol. 2488, Springer-Verlag.

Muratore, Diane M. et al., "Beam Calibration Without a Phantom for Creating a 3D Free-hand Ultrasound System," Ultrasound in Medicine and Biology, 2001, pp. 1557-1566, vol. 27—No. 11, Elsevier.

Nakakura, Eric K et al., "Hepatocellular Carcinoma: Current Management Recommendations," Advances on Oncology, 2000, pp. 12-18, vol. 16—No. 2.

Nelson, Thomas R. et al., "Interactive Acquisition, Analysis, and Visualization of Sonographic Volume Data," International Journal of Imaging Systems and Technology, 1997, pp. 26-37, vol. 8, John Wiley & Sons, Inc.

Nelson, Thomas, R. et al., "Three-dimensional ultrasound imaging," Ultrasound in Medicine & Biology, 1998, pp. 1243-1270, vol. 24—No. 9, Elsevier.

Novotny Paul M. et al., "Tool Localization in 3D Ultrasound Images," Medical Image Computing and Computer-Assisted Intervention, 2003, pp. 969-970, vol. 2879, Springer.

Office Action mailed Jun. 20, 2013 for Japanese Application No. 20110272386 filed Dec. 13, 2011, 8 pages.

Office Action mailed Dec. 27, 2013 for Japanese Application No. 20110272386 filed Dec. 13, 2011, 8 pages.

Office Action mailed Jul. 31, 2014 for Japanese Application No. 2013-194017 filed Sep. 19, 2013.

Ohbuchi, Ryutarou et al., "Incremental vol. Reconstruction and Rendering for 3D Ultrasound Imaging," The International Society of Optical Engineering, 1992, pp. 312-323, vol. 1808, SPIE.

Park, Shinsuk et al., "Virtual Fixtures for Robotic Cardiac Surgery," Proceedings of the 4th International Conference on Medical Image Computing and Computer-Assisted Intervention, 2001, pp. 1419-1420, vol. 2208, Springer-Verlag.

Patriciu Alexandru et al., "Motion-based robotic instrument targeting under c-arm fluoroscopy," Medical Image Computing and Computer-Assisted Interventions, 2000, pp. 988-998, vol. 1935, Springer.

Podnos, Yale, D. et al., "Laparoscopic Ultrasound with Radiofrequency Ablation in Cirrhotic Patients with Hepatocellular Carcinoma," Am Surg, 2001, pp. 1181-1184, vol. 67—No. 12.

Poulose P. K et al., "Human vs Robotic Organ Retraction During Laparoscopic Nissen Fundoplication," Surgical Endoscopy, 1999, pp. 461-465, vol. 13, Springer-Verlag.

Prager Richard et al., "Practical segmentation of 3D ultrasound," In Proceedings of Medical Image Understanding and Analysis, 1999, pp. 161-164.

Prager Richard et al., "Rapid Calibration for 3D Freehand Ultrasound," Ultrasound in Medicine and Biology, 1998, pp. 855-869, vol. 24—No. 6, Elsevier.

Prasad, Srinivas K. et al., "A minimally invasive approach to pelvic osteolysis," 2002, in Proc. Computer-Assisted Orthopaedic Surgery (CAOS), pp. 349-350.

Prasad Srinivas K. et al., "A Modular 2-DOF Force-Sensing Instrument for Laparoscopic Surgery," Proceedings of the Sixth International Conference on Medical Image Computing and Computer Assisted Intervention—MICCAI, Lecture Notes in Computer Science, 2003, pp. 279-286, vol. I, Springer.

Ramey, Nicholas A. et al., "Evaluation of Registration Techniques in a robotic approach to pelvic osteolysis," International Proceedings of Computer Assisted Orthopaedic Surgery (CAOS), 2004, pp. 26-27.

Ramey, Nicholas A., "Stereo-Based Direct Surface Tracking with Deformable Parametric Models," 2003, 104 Pages Total.

Rasmussen, Christopher et al., "Probabilistic data association methods for tracking complex visual objects," IEEE Transactions on Pattern Analysis and Machine Intelligence, 2001, pp. 560-576, vol. 23, Issue 6, IEEE.

Ratner, Lloyd E. et al, "Laparoscopic live donor nephrectomy removes disincentives to live donation," Transplantation, 1997, pp. 3402-3403, vol. 29—Issue 8, Elsevier.

Ratner, Lloyd E. et al., "Laparoscopic live donor nephrectomy," Transplantation, 1995, pp. 1047-1049.

Rau, Beate, M. eta al., "Is There Additional Information From Laparoscopic Ultrasound in Tumor Staging", Digestive Surgery, 2002, pp. 479-483, vol. 19—No. 6.

Rockall, Timothy A., "The da Vinci Telerobotic Surgical System," Chapter 8 in Primer of Robotic & Telerobotic Surgery, Eds. Garth H. Ballantyne et al., Pub. By Lippincott Williams & Wilkins, Philadelphia, 2004, pp. 57-60.

Rohling, Robert et al., "Three-dimensional spatial compounding of ultrasound images," Medical Image Analysis, 1996, pp. 177-193, vol. 1—No. 3, Oxford University Press.

Rohling, Robert N. et al., "Radial basis function interpolation for 3-d ultrasound," CUED/F-INFENG/TR 327, Cambridge University, Jul. 1998, 28 Pages.

Rosen, Jacob et al., "The BlueDRAGON—A System for Measuring the Kinematics and the Dynamics of Minimally Invasive Surgical Tools In-Viva," Proceedings of the 2002 IEEE International Conference on Robotics 8 Automation, 2002, pp. 1876-1881, IEEE.

Rosenberg, Louis B., "Virtual Fixtures: Perceptual Tools for Telerobotic Manipulation," IEEE Virtual Reality International Symposium, 1993, pp. 76-82, IEEE.

Rothbaum Daniel L. et al., "Robot-assisted stapedotomy: micropick fenestration of the stapes footplate," Otolaryngology—Head and NeckSurgery, 2002, pp. 417-426, vol. 127.

Rothbaum Daniel L. et al., "Task Performance in stapedotomy: Comparison between surgeons of different experience levels," Otolaryngology—Head and Neck Surgery, 2003, pp. 71-77, vol. 128—No. 1.

Roy, Jaydeep, "Advances in the design, analysis and control of force controlled robots," Master's Thesis, Mechanical Engineering, Johns Hopkins University, Baltimore, 2001, 210 Pages.

Sakas, Georgios et al., "Extracting surfaces from fuzzy 3D-Ultrasound data," Proceedings of the 22nd annual conference on Computer graphics and interactive techniques, 1995, pp. 465-474.

Salcudean, Septimiu E. et al., "A Robot System for Medical Ultrasound," 9th International Symposium of Robotics Research (ISRR'99), 1999, pp. 195-202.

Santambrogio, R. et al., "Ultrasound-Guided Interventional Procedures of the Liver During Laparoscopy: Technical Considerations," Surg Endosc, 2002, pp. 349-354, Springer-Verlag.

Schorr, Oliver et al., "Distributed Modular Computer-Integrated Surgical Robotic Systems: Architecture for Intelligent Object Distribution," Proceedings of the Third International Conference on Medical Image Computing and Computer-Assisted Intervention, Lecture Notes in Computer Science, 2000, pp. 979-978, vol. 1935, Springer.

Schreiner, Steve et al., "A system for percutaneous delivery of treatment with a fluoroscopically-guided robot," Proceedings of the First Joint Conference on Computer Vision, Virtual Reality and Robotics in Medicine and Medial Robotics and Computer-Assisted Surgery, Lecture Notes in Computer Science, 1997, pp. 747-756, Springer-Verlag.

Schweikard, Achim et al., "Motion Planning in Stereotaxic Radiosurgery," IEEE Transactions on Robotics and Automation, 1993, pp. 909-916, vol. 1, IEEE.

Scott, D.J., "Accuracy and Effectiveness of Laparoscopic vs. Open Hepatic Radiofrequency Ablation," Surg Endosc, 2001, pp. 349-354, vol. 16—No. 2, Springer.

Shahram, Payandeh, et al., "On Application of Virtual Fixtures as an Aid for Telemanipulation and Training," IEEE 10th Symposium on Haptic Interfaces for Virtual Environment and Teleoperator systems, Mar. 24-25, 2002, pp. 18-23, IEEE.

Simaan, Nabil et al., "A Dexterous System for Laryngeal Surgery: Multi-Backbone Bending Snake-like Slaves for Teleoperated Dextrous Surgical Tool Manipulation," IEEE International Conference on Robotics and Automation, 2004, pp. 351-357, IEEE.

Simaan, Nabil et al., "High Dexterity Snake-Like Robotic Slaves for Minimally Invasive Telesurgery of the Upper Airway," MICCAI 2004—the 7th International Conference on Medical Image Computing and Computer-Assisted Intervention, 2004, pp. 17-24.

(56) References Cited

OTHER PUBLICATIONS

Solomon, Stephen B. et al., "CT Guided Robotic Needle Biopsy: A Precise Sampling Method Minimizing Radiation Exposure to the Physician, Radiology," 2002, pp. 277-282, vol. 225.

Solomon, Stephen B. et al., "Robotically Driven Interventions: A Method of Using CT Fluoroscopy without Radiation Exposure to the Physician," Radiology, 2002, pp. 277-282, vol. 225.

Solus -3D web site: Last updated Jun. 24, 1999; downloaded Jul. 5, 2007.

Sommer, Graham et al., "Liver tumors: utility of characterization at dual frequency US," Radiology, 1999, pp. 629-636, vol. 211—No. 3.

Steele, Micah R. et al., "Shared control between human and machine: using a haptic steering wheel to aid in land vehicle guidance," Human Factors and Ergonomics Society 45th Annual Meeting, Minneapolis, Minnesota, 2001, pp. 1671-1675.

Steen, Erik et al., "Volume Rendering of 3D Medical Ultrasound Data Using Direct Feature Mapping," IEEE Transactions on Medical Imaging, 1994, pp. 517-525, vol. 13—Iss. 3, IEEE.

Stefansic, James D. et al., "Registration of Physical Space to Laparoscopic Image Space for Use in Minimally Invasive Hepatic Surgery," IEEE Transactions on Medical Imaging, 2000, pp. 1012-1023, vol. 19—No. 10, IEEE.

Stetten, George D et al., "Overlaying Ultrasound Images on Direct Vision," Journal of Ultrasound in Medicine, 2001, pp. 235-240, vol. 20—No. 3.

Stewart, Charles V. et al., "The Dual-Bootstrap Iterative Closest Point Algorithm With Application to Retinal Image Registration," IEEE Transactions on Medical Imaging, Nov. 2003, pp. 1379-1394, vol. 22—No. 11, IEEE.

Stoianovici, Dan et al., "Robotic for Precise Percutaneous Needle Insertion," In Thirteenth Annual Meeting of the Society for Urology and Engineering. San Diego, May 1998, pp. 4.

Stoianovici, Dan et al., "Robotic Telemanipulation for Percutaneous Renal Access," 16th World Congress on Endourology, 1998, pp. S201.

Stoll, Jeff, "Ultrasound-based servoing of manipulators for telesurgery," Telemanipulator and Telepresence Technologies VIII Conference, 2001, pp. 78-85, SPIE.

Sublett, John W. et al. "Design and implementation of a digital teleultrasound system for real-time remote diagnosis," 8th IEEE Symposium on Computer-Based Medical Systems, IEEE Computer Society Press, Jun. 9-10, 1995, pp. 292-298.

Suramo, I. et al., "Cranio-caudal movements of the liver, pancreas and kidneys in respiration," Acta Radiologica: Diagnosis, 1984, pp. 129-131, vol. 25, Radiological Societies.

Susil, Robert, C. et al., "A Single Image Registration Method for CT Guided Interventions," 2nd International Symposium on Medical Image Computing and Computer-Assisted Interventions (MICCAI' 99),Lecture Notes in Computer Science, 1999, pp. 798-808, vol. 1679, Springer-Verlag.

Szeliski, Richard, "Motion Estimation with Quadtree Splines," IEEE 5th International Conference on Computer Vision, 1995, pp. 757-763, vol. 18—Issue. 12, IEEE Computer Society Washington, DC, USA.

Taylor, Russell H., "A Perspective on Medical Robotics," Proceedings of the IEEE, vol. 94, No. 9, Sep. 2006, pp. 1652-1664.

Taylor, Russell H. "An Image-directed Robotic System for Precise Orthopaedic Surgery," IEEE Transactions on Robotics mid Automation, 1994, pp. 261-275, vol. 10—No. 3, IEEE.

Taylor, Russell H. and Christopher Hasser, "Development of a Surgical Assistant Workstation for Teleoperated Surgical Robots," NSF Proposal No. 0646678, Aug. 2006, 16 pages.

Taylor, Russell H. and Dan Stoianovici, "Medical Robotic Systems in Computer-Integrated Surgery," Problems in General Surgery, by Lippincott Williams & Wilkins, Inc., Philadelphia, Pennsylvania. vol. 20, No. 2, pp. 1-9, 2003.

Taylor, Russell H. and Peter Kazanzides, "Medical Robotics and Computer-Integrated Interventional Medicine," Chapter 18: Biomedical Information Technology, David Dagan Feng, Ed., Academic Press (Elsevier), 2008, pp. 393-416.

Taylor, Russell H. et al., "A Computational Architecture for Programmable Automation Research," Conference on Intelligent Robots and Computer Vision, 1986, pp. 438-440, vol. 726, SPIE.

Taylor, Russell H. et al., "A General Purpose Control Architecture for Programmable Automation Research," Proceedings of the Third International Symposium on Robotics, 1986, pp. 165-174, MIT Press.

Taylor, Russell, H et al., "A Steady-Hand Robotic System for Microsurgical Augmentation," International Journal of Robotics Research, 1999, pp. 1201-1210, vol. 18—No. 12, Springer-Verlag.

Taylor, Russell H. et al., "A Telerobotic System for Augmentation of Endoscopic Surgery," in IEEE Conference on Engineering in Medicine and Biology, vol. 14, 1992, pp. 1054-1056, vol. 3, IEEE.

Taylor, Russell, H et al., "AML A Manufacturing Language," The International Journal of Robotics Research, 1982, pp. 19-41, vol. 1—No. 3, Sage Publications.

Taylor, Russell H. et al., "An Image-directed Robotic System for Hip Replacement Surgery," J. Robotics Society of Japan, 1990, pp. 615-620, vol. 8—issue 5.

Taylor, Russell, H. et al., "An Integrated Robot Systems Architecture," Proceedings of the IEEE, 1983, pp. 842-856, vol. 71—Issue 7, IEEE.

Taylor, Russell H., et al., "An overview of computer-integrated surgery at the IBM Thomas J. Watson Research Center," IBM J Research and Development, 1996, pp. 163-183, vol. 40, Issue 2, IBM Corp.

Taylor, Russell H., et al., "Chapter 46: A Telerobotic Assistant for Laparoscopic Surgery," in Computer-Integrated Surgery, R. H. Taylor, et al., Editors, 1996, MIT Press. pages 581-592.

Taylor, Russell H. et al., "Computer-Integrated Revision Total Hip Replacement Surgery: Concept and Preliminary Results," 1999, Medical image analysis, pp. 301-319, vol. 3—Issue 3, Oxford University Press.

Taylor, Russell H. et al., "Computer-Integrated Surgery," 1996, 8 Pages, MIT Press.

Taylor, Russell H. et al., "Medical Robotics and Computer-Integrated Surgery," Chapter 52 in Springer Handbook of Robotics, Springer, 2008, pp. 1199-1222.

Taylor, Russell H. et al., "Medical Robotics in Computer-Integrated Surgery," IEEE Transactions on Robotics and Automation, 2003, pp. 765-781, vol. 19—No. 5, IEEE.

Taylor, Russell, H. et al., "Redundant Consistency Checking in a Precise Surgical Robot," in 12'th Annual Conference on Engineering in Medicine and Biology, 1990, pp. 1933-1935, vol. 12—No. 5, IEEE.

Taylor, Russell, H et al., "The Architecture of an Integrated Robot System," First Int. Conf. on Advanced Robotics (ICAR)., 1983, pp. 389-398.

Taylor, Russell H. "Medical Robotics and Computer-Integrated Surgery," Handbook of Industrial Robotics, Second Edition, 1999, pp. 1213-1230, Chapter 65, John Wiley & Sons.

Taylor, Russell H. "Medical Robots," in Computer and Robotic Assisted Knee and Hip Surgery, 2004, pp. 54-59, Oxford Press.

Taylor, Russell H., "Robotics in Orthopedic Surgery," In Computer Assisted Orthopaedic Surgery (CAOS), L.P. Nolte and R. Ganz, Editors. 1999, Hogrefe and Huber, 1999, pp. 35-41.

Taylor, Russell H. "The Planning and Execution of Straight Line Manipulator Trajectories," IBM Journal of Research and Development, 1979, pp. 424-436, vol. 23—Issue 4.

Taylor, Russell H., "Ultrasound Assistant for a Laparoscopic Surgical Robot," NIH STTR Phase II Proposal R42-RR019159, revised May 2001, 54 pages.

Taylor, Russell H., Videotape: "Computer Assisted Surgery at IBM T. J. Watson Research Center," 22 minutes 10 seconds, 1994 and 1995.

Teistler, Michael et al., "Virtual Tomography: A New Approach to Efficient Human-Computer Interaction for Medical Imaging," Proc. of SPIE,, The International Society for Optical Engineering (SPIE), Medical Imaging 2003: Visualization, Image-Guided Procedures, and Display; San Diego, CA, Ed. Robert L. Galloway, 2003, pp. 512-519, vol. 5029.

Tewari, Ashutosh et al., "Technique of da Vinci Robot-Assisted Anatomic Radical Prostatectomy," Urology, 2002, pp. 569-72,vol. 60—No. 4, Elsevier.

(56) References Cited

OTHER PUBLICATIONS

Toyama, Kentaro et al., "Incremental Focus of Attention for Robust Visual Tracking," International Journal of Computer Vision, 1999, pp. 45-63, vol. 35—No. 1, Kluwer Academic Publishers.

Troccaz, Jocelyne et al., "The use of localizers, robots, and synergistic devices in CAS," Proceedings of the First Joint Conference on Computer Vision, Virtual Reality and Robotics in Medicine and Medial Robotics and Computer-Assisted Surgery,Lecture Notes in Computer Science, 1997, pp. 727-736, vol. 1205, Springer-Verlag.

Uecker, Darrin R. et al., "A Speech-Directed Multi-Modal Man-Machine Interface for Robotically Enhanced Surgery," 1994, pp. 176-183.

Umeyama, Shinji, "Least-Squares Estimation of Transformation Parameters between Two Point Patterns," IEEE Transactions on Pattern Analysis and Machine Intelligence (PAMI), vol. 13, No. 4, pp. 376-380, Apr. 1991.

U.S. Appl. No. 11/583,963 Non-Final Office Action mailed Jul. 9, 2009, 40 pages.

Vilchis, Adriana et al., "A New Robot Architecture for Tele-Echography," IEEE Trans. Robotics & Automation, pp. 922-926, 2003, vol. 19—No. 5, IEEE.

Viswanathan, Anand et al., "Immediate Ultrasound Calibration with Three Poses and Minimal Image Processing," MICCAI, 2004, pp. 446-454, vol. 2, Springer-Verlag.

Webster Robert J. et al., "Design Considerations for Robotic Needle Steering," International Conference on Robotics and Automation, 2005, pp. 3588-3594, IEEE.

Webster Robert J. et al "Nonholonomic Modeling of Needle Steering," The International Journal of Robotics Research, 2004, pp. 509-525, vol. 25—No. 5-6, SAGE Publications.

Wei, Zhouping et al "Robot-assisted 3D-TRUS guided prostate brachytherapy: system integration and validation," Medical Physics, 2004, pp. 539-548, vol. 31—No. 3.

Wilhelm, Dirk et al., "Electromagnetically Navigated Laparoscopic Ultrasound," Surg. Technol. Int, 2003, pp. 50-54, vol. 11.

Wood Thomas F. et al., "Radiofrequency ablation of 231 Unresectable hepatic tumors:indications, limitations, and complications," Ann. Surg. Oncol, 2000, pp. 593-600, vol. 7, Lippincott Williams & Wilkins.

Wu, Xiaohui et al., "A Framework for Calibration of Electromagnetic Surgical Navigation Systems," IEEE RSJ International Conference on Intelligent Robot Systems (IROS), 2003, pp. 547-552, vol. 1, IEEE.

Xu, Sheng et al., "3D Motion Tracking of Pulmonary Lesions Using CT Fluoroscopy Images for Robotically Assisted Lung Biopsy," International Society of Optical Engineering, 2004, pp. 394-402, SPIE.

Yamagata, Hitoshi, "Development of a New Display Method for Compound 3D Ultrasound Images: Fusion 3D Images From B-mode and 3D Doppler Images," 1999, pp. 43-46, vol. 70.

Yao, Jianhua et al., "A C-arm fluoroscopy-guided progressive cut refinement strategy using a surgical robot," Computer Aided Surgery, 2000, pp. 373-390, vol. 5—No. 6, Wiley-Liss, Inc.

Yao, Jianhua, et al., "A Progressive Cut Refinement Scheme for Revision Total Hip Replacement Surgery Using C-arm Fluoroscopy," Proceedings of the 2nd International Conference on Medical Image and Computer-Assisted Intervention (MICCAI'99), Springer-Verlag, 1999, pp. 1010-1019, vol. 1679.

Yao, Jianhua et al., "Deformable registration between a statistical born density atlas and X-ray images," Second International Conference on Computer Assisted Orthopaedic Surgery, 2002, pp. 168-169.

Zacherl, Johannes et al., "Current value of intraoperative sonography during surgery for hepatic neoplasms," World J Surg, 2002, pp. 550-554, vol. 26—No. 5.

Zhang, Zhengyou, "A Flexible New Technique for Camera Calibration," 1998, pp. 1-21.

Cleary, Kevin et al., "State of the Art in Surgical Robotics:Clinical Applications and Technology Challenges," Computer Aided Surgery, 2001 [retrieved on Feb. 24, 2002], pp. 1-26.

Cleary, Kevin et al., "State of the art surgical robotics clinical applications and technology challenges," Computer Aided Surgery, 2001, pp. 312-328, vol. 6; Part 6, John Wiley & Sons.

Ganssle J.G. "A Guide to Debouncing", The Ganssle Group, Jun. 2008, 26 pages.

Madhani, Akhil J., "Design of Teleoperated Surgical Instruments for Minimally Invasive Surgery," Feb. 1998, pp. 1-251.

Office Action mailed Jun. 12, 2015 for Japanese Application No. 20130186992 filed Sep. 10, 2013, 8 pages.

Stoianovici, Dan, "A Modular Surgical Robotic System for Image Guided Percutaneous Procedures," Proceedings of the First International Conference on Medical Image Computing and Computer-Assisted Intervention, pp. 404-410, vol. 1496, Springer-Verlag, 1998.

Wengert, Christian, "Camera Calibration Toolbox for Matlab," [online][retrieved on Oct. 24, 2006], Retrieved from the Internet: <URL:http://www.vision.caltech.edu/bouguetj/calib_doc/>, 5 pages.

\* cited by examiner

REAL-TIME GENERATION OF THREE-DIMENSIONAL ULTRASOUND IMAGE USING A TWO-DIMENSIONAL ULTRASOUND TRANSDUCER IN A ROBOTIC SYSTEM

CROSS REFERENCE TO RELATED APPLICATIONS

This application is a divisional of U.S. application Ser. No. 11/093,372 filed Mar. 30, 2005, which is incorporated herein by reference.

U.S. application Ser. No. 11/093,372 is a continuation-in-part of U.S. application Ser. No. 10/314,001 filed Dec. 5, 2002, now U.S. Pat. No. 7,107,090, which is a continuation of U.S. application Ser. No. 09/464,455 filed Dec. 14, 1999, now U.S. Pat. No. 6,522,906, which is a continuation-in-part of U.S. application Ser. No. 09/457,406, filed Dec. 7, 1999, now U.S. Pat. No. 6,799,065, each of which is incorporated herein by reference.

U.S. application Ser. No. 11/093,372 is additionally a continuation-in-part of U.S. application Ser. No. 10/644,406, filed Aug. 19, 2003, now abandoned, which is a continuation of U.S. application Ser. No. 10/163,626, filed Jun. 5, 2002, now U.S. Pat. No. 6,671,581, which is a continuation of U.S. application Ser. No. 09/373,678, filed Aug. 13, 1999, now U.S. Pat. No. 6,424,885, which claims benefit of U.S. Provisional Application No. 60/128,160, filed Apr. 7, 1999, each of which is incorporated herein by reference.

BACKGROUND OF THE INVENTION

The present invention is generally related to improved robotic devices, systems and methods, for use in telerobotic surgery.

Minimally invasive medical techniques are aimed at reducing the amount of extraneous tissue which may be damaged during diagnostic or surgical procedures, thereby reducing patient recovery time, discomfort, and deleterious side effects. Many surgeries are performed each year in the United States. A significant amount of these surgeries can potentially be performed in a minimally invasive manner. However, only a relatively small percentage of surgeries currently use minimally invasive techniques due to limitations of minimally invasive surgical instruments and techniques currently used and the difficulty experienced in performing surgeries using such traditional instruments and techniques.

Advances in minimally invasive surgical technology could dramatically increase the number of surgeries performed in a minimally invasive manner. The average length of a hospital stay for a standard surgery is significantly longer than the average length for the equivalent surgery performed in a minimally invasive surgical manner. Thus, expansion in the use of minimally invasive techniques could save millions of hospital days, and consequently millions of dollars annually, in hospital residency costs alone. Patient recovery times, patient discomfort, surgical side effects, and time away from work can also be reduced by expanding the use of minimally invasive surgery.

Traditional forms of minimally invasive surgery include endoscopy. One of the more common forms of endoscopy is laparoscopy, which is minimally invasive inspection or surgery within the abdominal cavity. In traditional laparoscopic surgery a patient's abdominal cavity is insufflated with gas and cannula sleeves are passed through small (approximately ½ inch) incisions in the musculature of the patient's abdomen to provide entry ports through which laparoscopic surgical instruments can be passed in a sealed fashion.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by an approximately 12-inch long extension tube, for example, so as to permit the surgeon to introduce the end effector to the surgical site and to control movement of the end effector relative to the surgical site from outside a patient's body.

To perform surgical procedures, the surgeon typically passes these working tools or instruments through the cannula sleeves to the internal surgical site and manipulates the instruments or tools from outside the abdomen by sliding them in and out through the cannula sleeves, rotating them in the cannula sleeves, levering (i.e., pivoting) the instruments against the abdominal wall and actuating the end effectors on the distal ends of the instruments from outside the abdominal cavity. The instruments normally pivot around centers defined by the incisions which extend through the muscles of the abdominal wall. The surgeon typically monitors the procedure by means of a television monitor which displays an image of the surgical site via the laparoscopic camera. Typically, the laparoscopic camera is also introduced through the abdominal wall so as to capture an image of the surgical site. Similar endoscopic techniques are employed in, e.g., arthroscopy, retropentoneoscopy, pelviscopy, nephroscopy, cystoscopy, cistemoscopy, sinoscopy, hysteroscopy, urethroscopy, and the like.

There are many disadvantages relating to such traditional minimally invasive surgical (MIS) techniques. For example, existing MIS instruments deny the surgeon the flexibility of tool placement found in open surgery. Difficulty is experienced in approaching the surgical site with the instruments through the small incisions. The length and construction of many endoscopic instruments reduces the surgeon's ability to feel forces exerted by tissues and organs on the end effector of the associated instrument. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment to the expansion of the use of minimally invasive surgery.

Minimally invasive telesurgical systems for use in surgery have been and are still being developed to increase a surgeon's dexterity as well as to permit a surgeon to operate on a patient in an intuitive manner. Telesurgery is a general term for surgical systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement during the surgical procedure on the visual display. While viewing typically a three-dimensional image of the surgical site on the visual display, the surgeon performs the surgical procedures on the patient by manipulating master control devices at the remote location, which master control devices control motion of the remotely controlled instruments.

Typically, such a telesurgery system can be provided with at least two master control devices (one for each of the surgeon's hands), which are normally operatively associated with two robotic arms on each of which a surgical instrument is mounted. Operative communication between master control devices and associated robotic arm and instrument assemblies is typically achieved through a control system. The control system typically includes at least one processor which relays input commands from the master control devices to the associated robotic arm and instrument assemblies and from the arm and instrument assemblies to the associated master control devices in the case of, e.g., force feedback, or the like.

One object of the present invention is to provide improved telesurgery systems, devices and methods for use in surgery. Another object of the invention is to provide a telesurgical system and method whereby auxiliary information related to a surgical procedure to be performed by the telesurgical system can be selectively displayed on a viewer of the system, together with an image of the surgical site captured by an image capture device, such as an endoscope, of the system, so as to enable an operator of the system selectively to reference such auxiliary information on the viewer during the performance of the surgical procedure. In this manner the surgical procedure can typically be performed with greater confidence, safety, efficacy and in some cases greater accuracy.

SUMMARY OF THE INVENTION

According to one aspect of the invention, there is provided a robotic system comprising: an ultrasound transducer; a robotic arm mechanically coupled to the ultrasound transducer; and a processor programmed to cause the robotic arm to move the ultrasound transducer so as to sweep a work site to obtain a plurality of spaced two-dimensional ultrasound images to provide sufficient information for construction of a three-dimensional model of at least a portion of the work site.

Additional objects, features and advantages of the various aspects of the present invention will become apparent from the following description of its preferred embodiment, which description should be taken in conjunction with the accompanying drawings.

DETAILED DESCRIPTION

Figure 1:
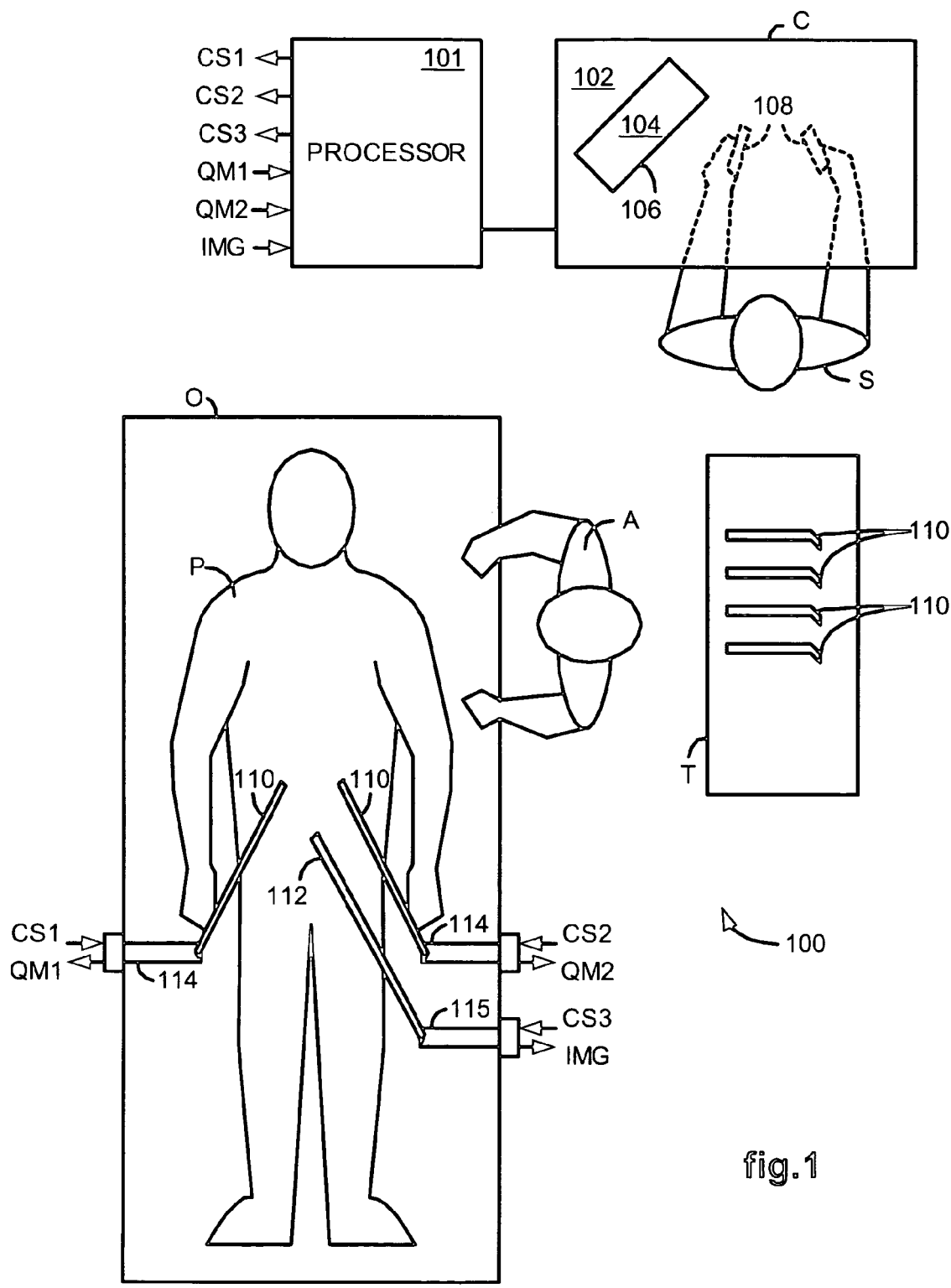
FIG. 1 illustrates a top view of an operating room employing a minimally invasive robotic telesurgical system.

FIG. 1 illustrates, as an example of a telesurgical system, a Minimally Invasive Robotic Surgical (MIRS) system 100 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a support 102, a monitor 104 for displaying an image of a surgical site to the Surgeon, and one or more control devices 108 (also referred to herein cumulatively as a "master manipulator"). The control devices 108 may include any one or more of a variety of input devices such as joysticks, gloves, trigger-guns, hand-operated controllers, or the like.

The Surgeon performs a procedure by manipulating the control devices 108 which in turn, cause robotic mechanisms 114 (also referred to herein as "slave manipulators") to manipulate their respective removably coupled instrument or tool assembly 110 (hereinafter simply referred to as a "tool") through a minimally invasive incision in the body of the Patient while the Surgeon views the surgical site through the monitor 104.

To manipulate the tools 110, each of the slave manipulators 114 is conventionally formed of linkages that are coupled together and manipulated through motor controlled joints. Since the construction and operation of such robotic manipulators are well known, their details need not be repeated here. For example, general details on robotic manipulators of this type can be found in John J. Craig, *Introduction to Robotics Mechanics and Control*, $2^{nd}$ edition, Addison-Wesley Publishing Company, Inc., 1989.

The number of surgical tools 110 used at one time and consequently, the number of robotic mechanisms 114 in the system 100 will generally depend on the diagnostic or surgical procedure and the space constraints within the operating room among other factors. If it is necessary to change one or more of the tools 110 being used during a procedure, the Assistant may remove the tool 110 no longer being used at the time from its robotic mechanism 114, and replace it with another tool 110 from a tray ("T") in the operating room.

The Surgeon's Console is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Preferably, control devices 108 will be provided with the same degrees of freedom as their associated tools 110 to provide the Surgeon with telepresence, or the perception that the control devices 108 are integral with the tools 110 so that the Surgeon has a strong sense of directly controlling the tools 110. To this end, position, force, and tactile feedback sensors are preferably employed on the tools 110 to transmit position, force, and tactile sensations from the tools 110 back to the Surgeon's hands as he/she operates the control devices 108.

A monitor 104 is suitably coupled to a viewing scope assembly 112, including one or more cameras, through a processor 101, and positioned on the support 102 of the Console such that an image of the surgical site is provided near the Surgeon's hands. Preferably, the monitor 104 will display a projected image on a display 106 that is oriented so that the surgeon feels that he or she is actually looking directly down onto the operating site. To that end, an image of the tools 110 appear to be located substantially where the operator's hands are located even though the observation points (i.e., the endoscope or viewing camera) may not be from the point of view of the image.

In addition, the real-time image is preferably projected into a perspective image such that the operator can manipulate the end effector of a tool 110 through its corresponding control device 108 as if viewing the workspace in substantially true presence. By true presence, it is meant that the presentation of an image is a true perspective image simulating the viewpoint of an operator that is physically manipulating the tools 110. Thus, the processor 101 (or another processor in the Console) transforms the coordinates of the tools 110 to a perceived position so that the perspective image is the image that one would see if the viewing scope assembly 112 was located directly behind the tools 110.

The processor 101 performs various functions in the system 100. One important function that it performs is to translate and transfer the mechanical motion of control devices 108 to robotic mechanisms 114 through control signals such as CS1 and CS2 so that the Surgeon ("S") can effectively manipulate the tools 110. Another important function is to provide force information to one or more force indicators so that the Surgeon and/or Assistant(s) may be informed, for example, if excessive force is being applied by a monitored tool that may harm or cause discomfort to the Patient. In providing such force information, it is important that it is done in such a manner so as to not significantly affect the stability of the telesurgical system 100. In particular, it should not drive the telesurgical system 100 unstable.

The force indicators, for example, may be integrated or attached to the support 102, and/or displayed on the monitor 104. Force indicators may also be activated on the control devices 108 in the form of vibration or viscous feel as described herein, provided the control devices 108 are equipped for such tactile sensations. Force indicators may also be placed so as to be proximate to or positioned on their respective slave manipulators 114.

The force information, for example, may be derived from strain gauge measurements on linkages in the slave manipulator manipulating the tool that is being monitored, or it may be derived from encoders associated with joints in the slave manipulator manipulating the tool that is being monitored. Typical processing to generate the force information may include filtering and/or gain adjustments.

The processor 101 may be separate from or integrated as appropriate into the robotic mechanisms 114 and 115, it may be or be part of a stand-alone unit, or it may be integrated in whole or in part into the Console serving as its processor or as a co-processor to its processor. Although described as a processor, it is to be appreciated that the processor 101 may be implemented in practice by any combination of hardware, software and firmware. Also, its functions as described herein may be performed by one unit, or divided up among different components, each of which may be implemented in turn by any combination of hardware, software and firmware.

Figure 2:
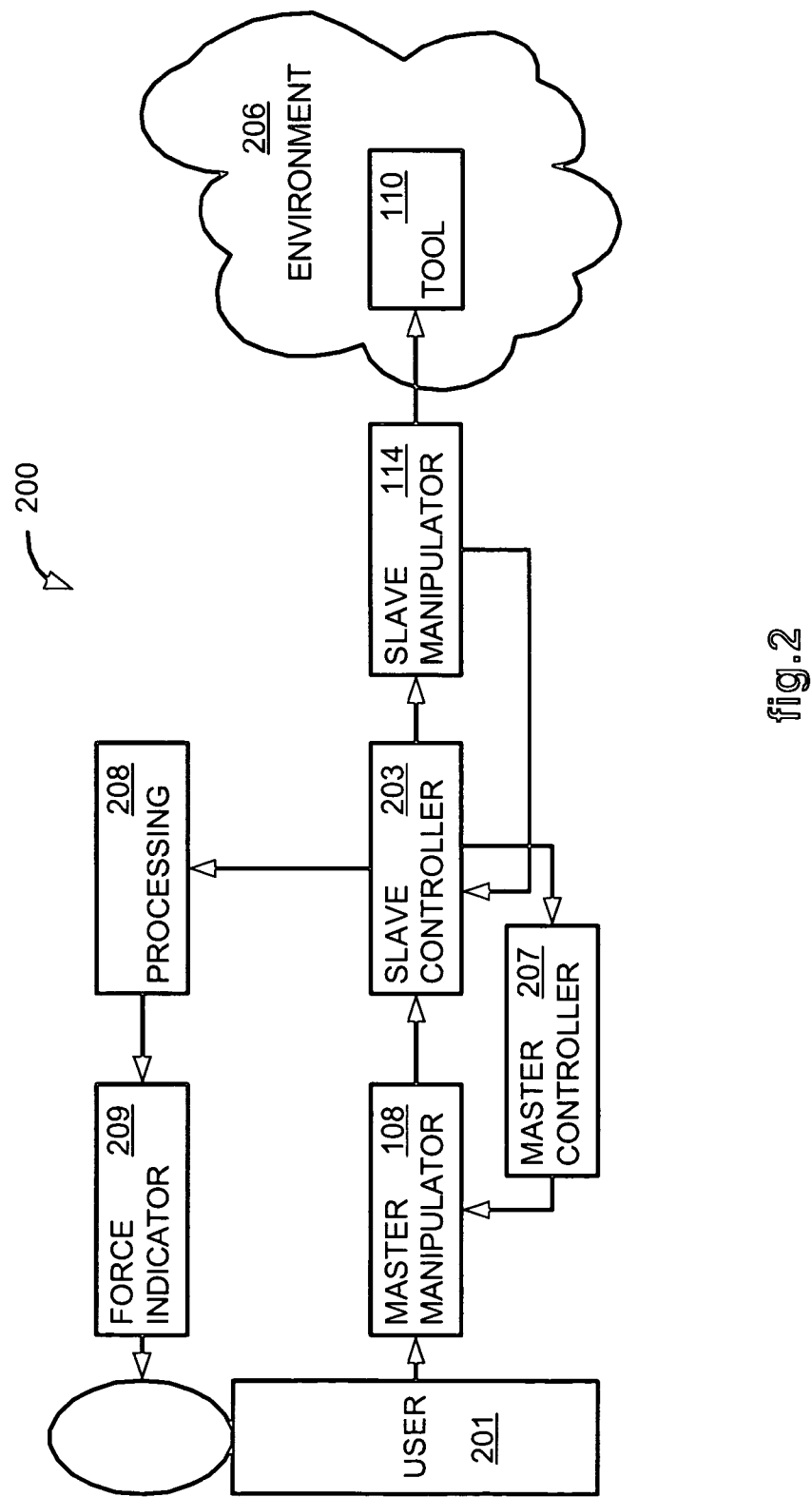
FIG. 2 illustrates a block diagram of a telesurgical system.

FIG. 2 illustrates, as an example, a block diagram of a telesurgical system 200 used in manipulating one of the tools 110 through its respective slave manipulator 114 in the MIRS system 100. The user 201 in this case is the Surgeon ("S") since it is the Surgeon ("S") who manipulates the master manipulator 108 in the MIRS system 100.

As the user 201 manipulates the master manipulator 108, the slave controller 203 translates its position from the coordinate frame of the master manipulator 108 to the coordinate frame of the tool 110. The slave controller 203 then determines the joint positions for the slave manipulator 114 that correspond to that tool position, and commands motors corresponding to each of those joints to move their respective joints to those positions using a closed-loop control system for each of the motors. Meanwhile, a master controller 207 feeds back any position error to the master manipulator 108 so that the master manipulator 108 tends to move in tandem along with the slave manipulator 114.

Figure 3:
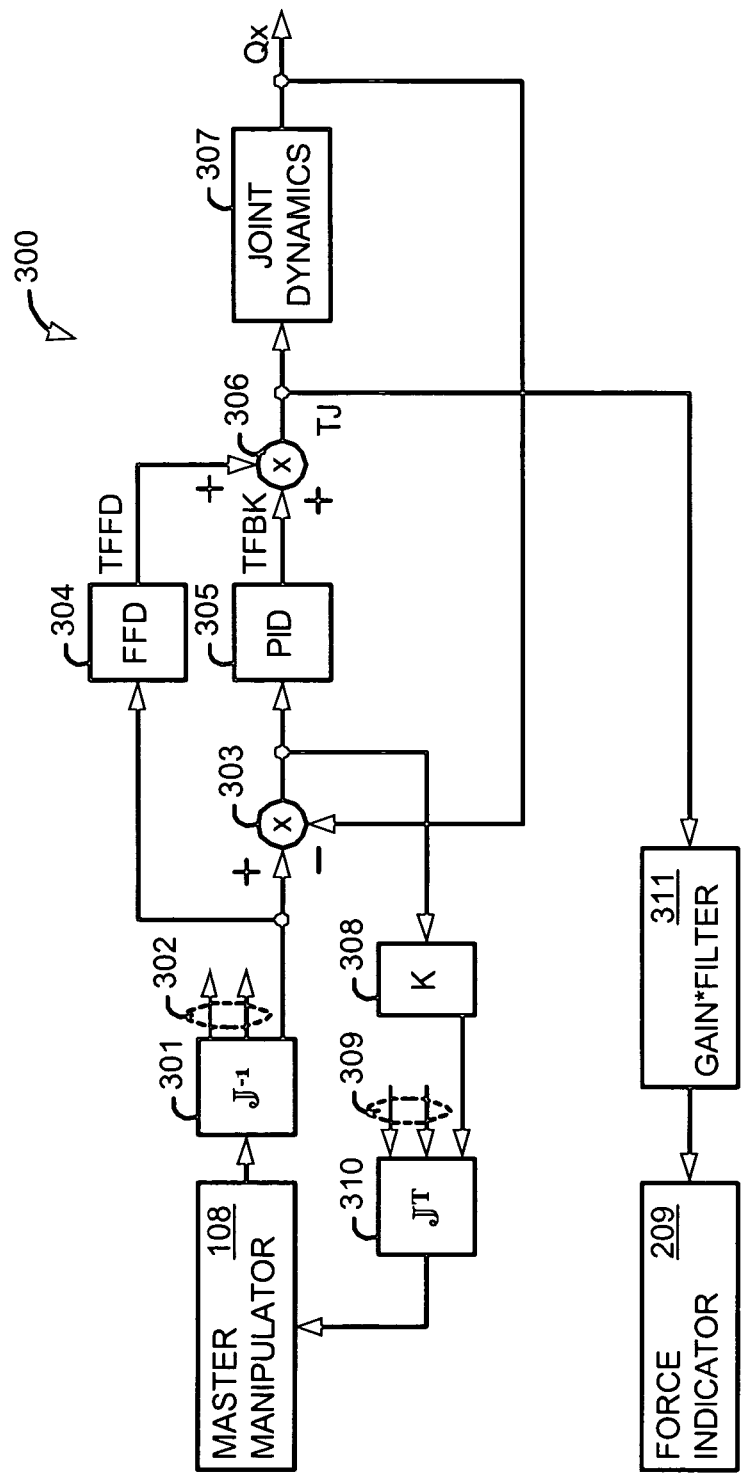
FIGS. 3-6 illustrate block diagrams of telesurgical systems using different joint torque values for tool force indication.

The functions of the slave controller 203 and the master controller 207 are implemented, for example, by programming them into a processor such as the processor 101 in the MIRS system 100. An example showing additional detail for such an implementation will now be described in reference to blocks 301-310 of FIG. 3. Referring to that figure, a closed-loop control system for driving a joint motor in the slave manipulator 114 is shown.

In this example, the closed-loop control includes a proportional, integral, derivative ("PID") function 305 and a feed-forward ("FFD") gain 304. Although a PID function is described herein, it is to be appreciated, however, that different control laws may also be implemented and are fully contemplated to be within the full scope of the various aspects of the present invention. As indicated by the sets of arrows 302 and 309, the master manipulator 108 is understood to also be driving other similarly configured closed-loop control systems corresponding to other joints of the slave manipulator 114.

The PID function 305 generates a feedback torque command ("TFBK") by operating on the joint position error between a commanded joint position from the inverse Jacobian 301 (ignoring coordinate transformations) and the detected joint position "Qx" from the joint encoder. The FFD gain 304 generates a feed-forward torque command ("TFFD") by operating on the commanded joint position, velocity, and acceleration. The feedback torque ("TFBK") and the feed-forward torque ("TFFD") are then added together to generate a total torque command ("TJ") that is applied to the joint motor, whose dynamics are depicted along with those of its joint in block 307, which is labeled JOINT DYNAMICS.

The joint position error is also provided to the master manipulator 108 through a gain ("K") 308 and transpose Jacobian 310. Although not shown to simplify the example, it is to be appreciated that a coordinate transformation from slave joint space to Cartesian space is also generally performed at this point. Since forces applied to the tool 110 such as a static force experienced when the tool 110 is pressing against an obstruction can create a joint position error, such reflected forces are effectively passed back to the master manipulator 108 by such position error being fed back.

One problem with the part of the telesurgical system described so far with respect to FIG. 2 is that additional filtering and/or gain to increase the sensitivity for detecting certain forces on the tool is difficult, since those changes may drive the joint closed-loop control systems incorporated therein to unstable conditions. As an example, if a relatively low level force is applied for an extended period of time by the tool against an obstruction such as the Patient's rib-cage, it may not be detected through the reflected forces being provided through the position error that is fed back to the master manipulator 108 due to a low value of the gain "K" 308 that is required to maintain system stability. As a consequence, bruising and/or prolonged discomfiture by the Patient during and/or after the minimally invasive surgical procedure may result.

Accordingly, referring back to FIG. 2 now, a force indicator 209 and processing unit 208 are added to the telesurgical system 200 to provide such types of tool force information to the user 201 without affecting the stability of the closed-loop control systems in the telesurgical system 200. In this case, the processing function 208 processes force or torque information received from the slave controller 203 substantially without restriction as to gain or filtering, because it is outside of the closed-loop control systems previously described herein.

Figure 4:
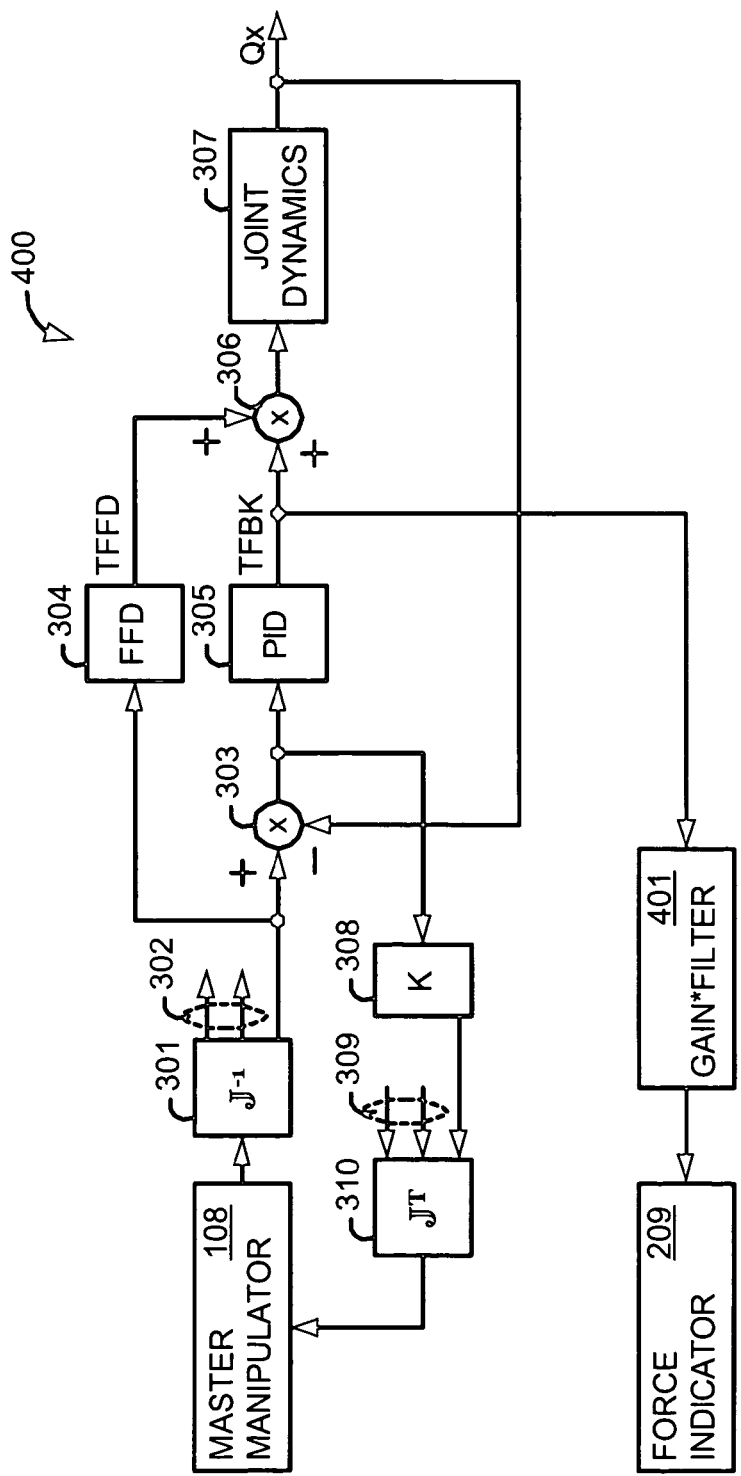
Figure 5:
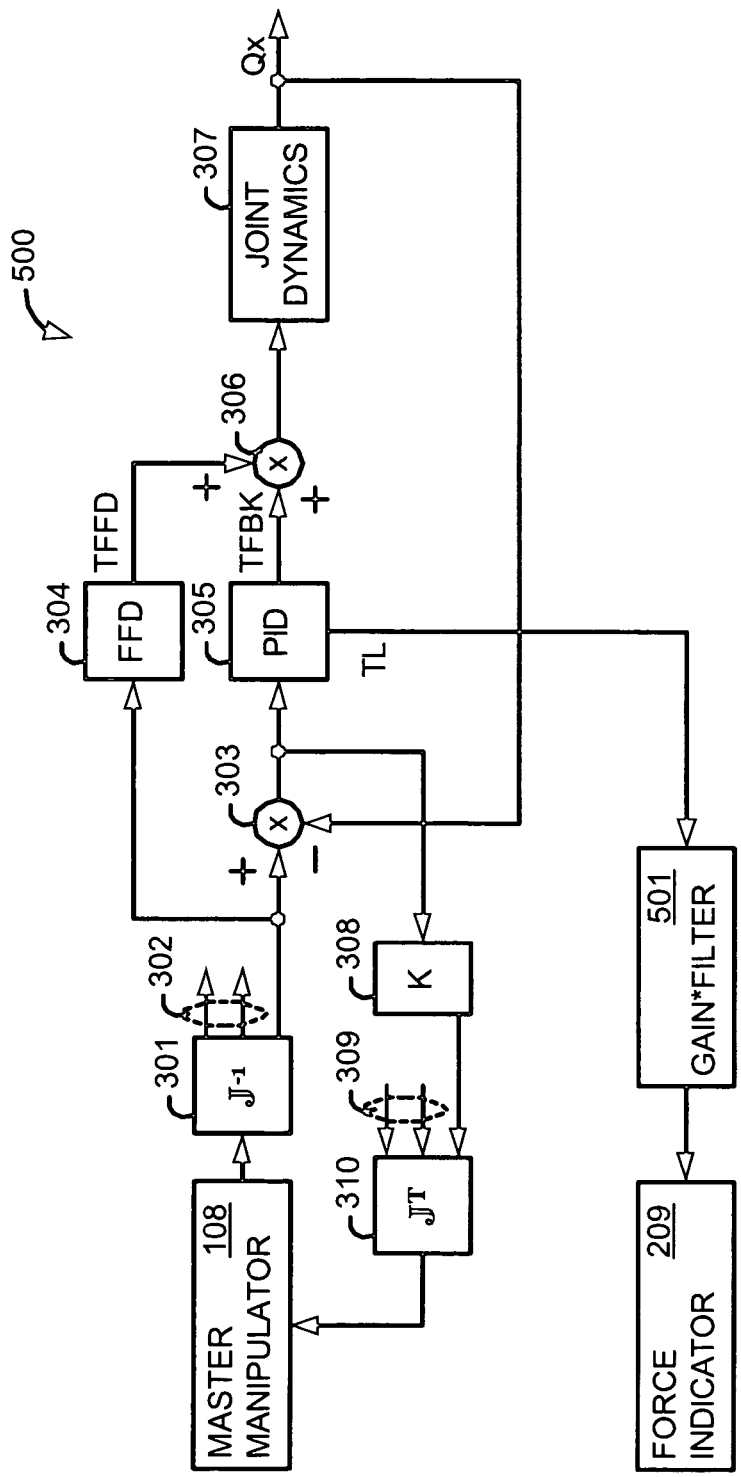
Figure 6:
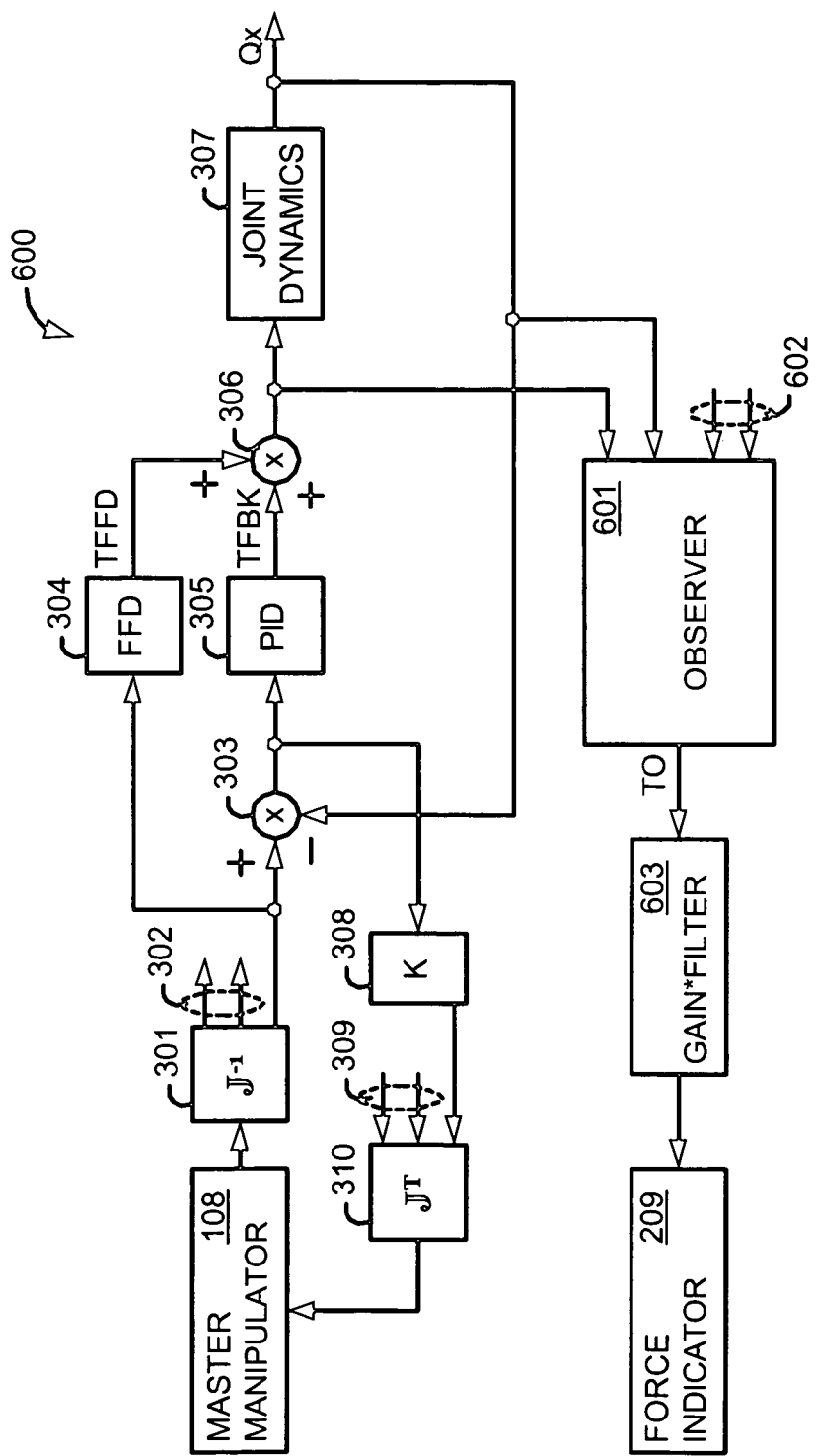
Figure 7:
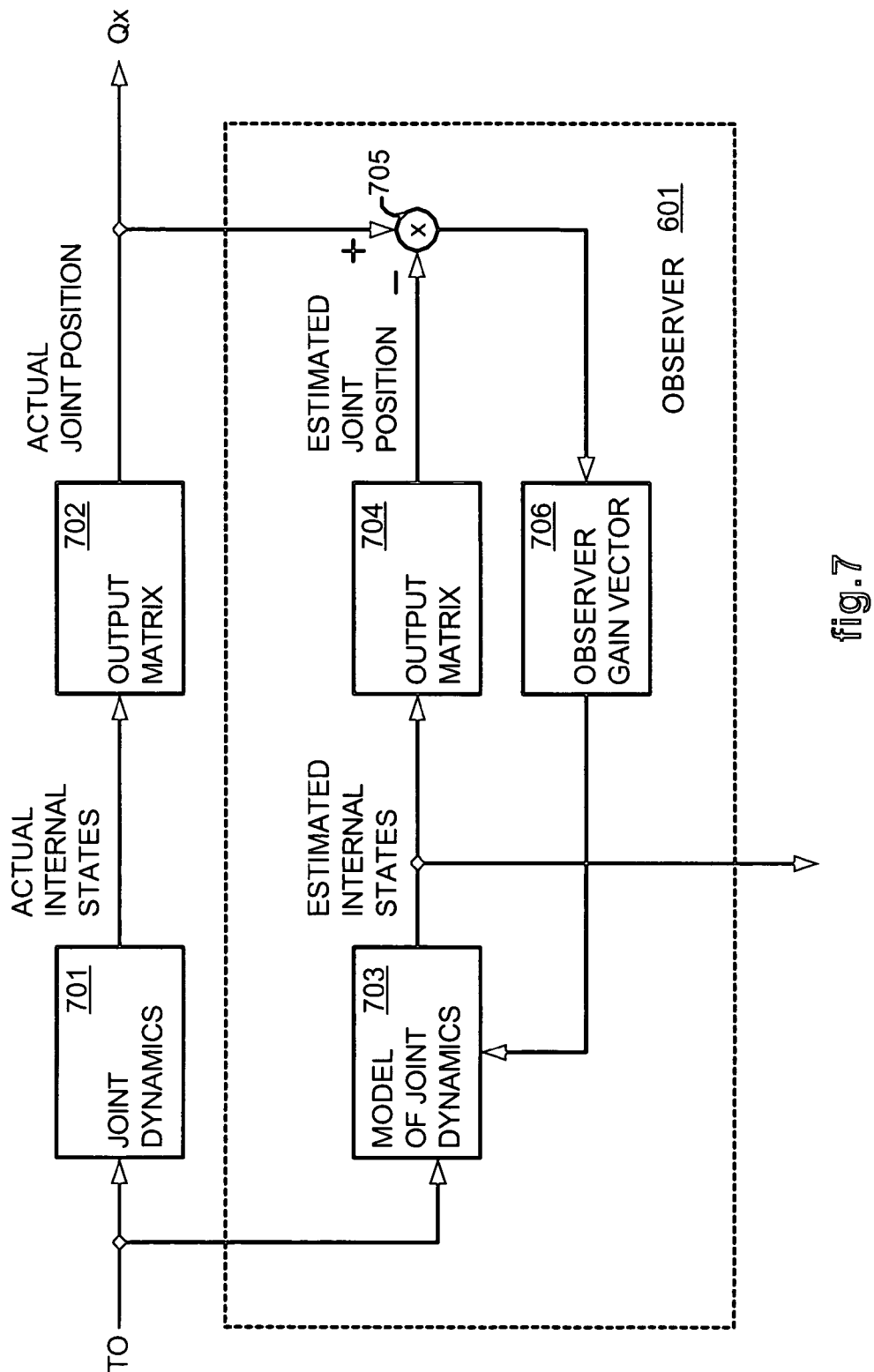
FIG. 7 illustrates a block diagram of an observer useful in the telesurgical system of FIG. 6.

As shown in FIGS. 3-6, the force or torque information from the slave controller 203 may be picked-off from several different points in the joint motor control systems. For example, in FIG. 3, the total joint torque ("TJ") command provided to the joint motor may be picked-off for generating the force information to be provided to the user 201 through the force indicator 209. In FIG. 4, the feedback torque ("TFBK") generated by the PID function 305 is picked-off for generating the force information. In FIG. 5, the integrator torque ("TL") from the integrator in the PID function 305 is picked-off for generating the force information. In FIG. 6, an observed disturbance torque "TO" that is generated by an observer 601 is used for generating the force information to be provided to the user 201 through the force indicator 209. An example of the observer 601 is illustrated FIG. 7. Since observers of this type are well-known in robotic control theory, detailed discussion of this figure is deemed unnecessary.

Note that depending upon the force that is to be presented to the user 201, the picked-off force locations may differ for different joints of the slave manipulator 114, and only selected ones of the joints may be tapped for picking off force or torque information. In addition, the gains and filters used for processing the picked-off force or torque values may be different for each of the joints. The processed force information thus picked off the joint control systems for the selected joints are then combined in an appropriate fashion before providing the force information to the user 201 through the force indicator 209.

The force indicator 209 may take any one of many different forms or modalities that is preferably turned-on or activated and turned-off or deactivated according to force threshold criteria. In the following examples, the force information is generated so as to determine a static force produced as the tool is pressed against an obstruction.

In one example of the force indicator 209, the force information may be provided to the user by turning on a user-visible indicator when information of the static force is greater than a first threshold value, and turning off the user-visible indicator when the information of the static force is less than a second threshold value. In this case, the first threshold value would generally be greater than the second threshold value.

One example of the user-visible indicator is a bar graph which may be displayed on the screen 106 of the monitor 104 of the MIRS system 100 so that it is visible to the user of the telesurgical system. In this case, as the static force asserted against the tool increases, the length of the bar graph increases accordingly.

Another example of the user-visible indicator is a blinking icon on the screen 106 of the monitor 104. Similarly, the user-visible indicator may be a flashing light on the support 102 of the Console or on the master manipulator 108 of the MIRS system 100 where the Surgeon would be able to readily see it, or the flashing light may be on or in the proximity of the slave manipulator 114 of the MIRS system 100 where the Surgeon and/or the Assistant(s) may be able to see it.

The color of the user-visible indicator may also change as the static force increases, such as going from green (indicating a safe level of force), to yellow (indicating a warning that the force is getting close to an unsafe or undesirable level), and to red (indicating an unsafe or undesirable level of force has been reached). In addition or alternatively to a change in color, the intensity of the user-visible indicator may change as the static force changes.

Another type of force indicator 209 is a user-audible indicator which preferably increases in intensity as the magnitude of the applied force increases. Another type of force indicator 209 uses haptic or tactile sensation features that may be implemented on the master manipulator 108, such as a haptic "buzz" that provides a buzzing sensation to the Surgeon while manipulating the master manipulator 108 or a haptic "viscosity" that makes operation of the master manipulator 108 feel more sluggish to the Surgeon. In the case of these tactile sensations being activated on the master manipulator 108, the frequency and/or amplitude of the "buzz" or the "viscosity" should be limited so as not to substantially affect the stability of the closed-loop control systems of the telesurgical system.

Figure 8:
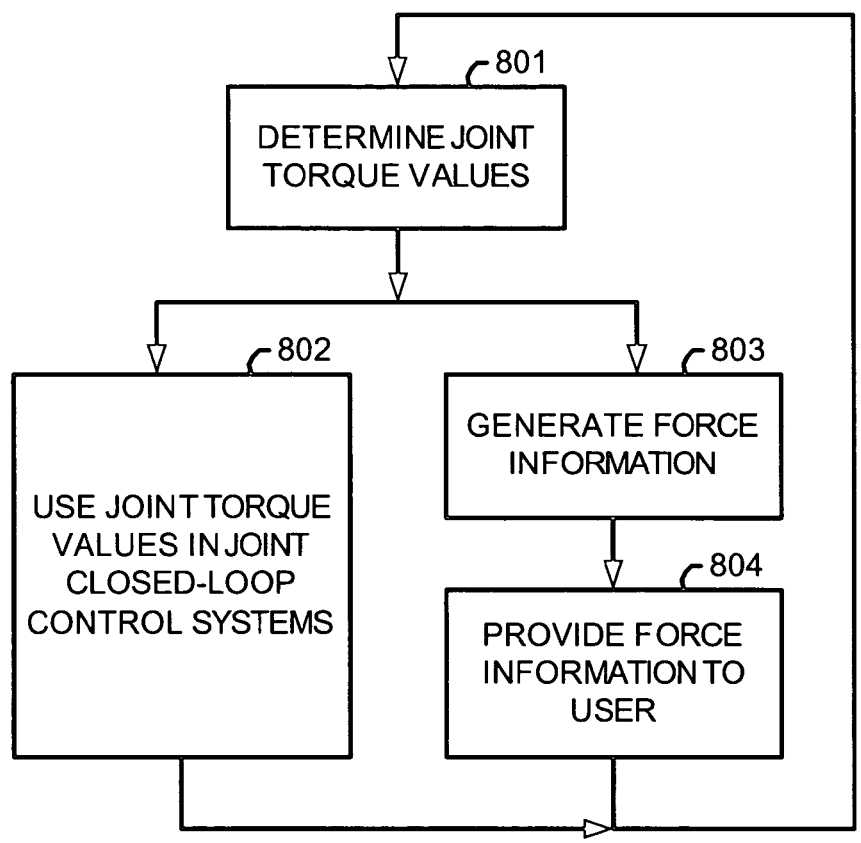
FIG. 8 illustrates a flow diagram of a method for providing force information to a user of a telesurgical system.

FIG. 8 illustrates a method for providing force information to the user 201 which is implemented, for example, by the addition of the force indicator 209 and the processing unit 208 to the telesurgical system 200. In 801, torque values are determined for joints employed in the telesurgical system for manipulating a tool. The torque values in this case are determined, for example, by the slave controller 203 processing the movement of the master manipulator 108 as manipulated by the user 201 (to determine TFFD, for example) and the movement of the joints of the slave manipulator 114 (to determine TFBK, for example).

The operation of the closed-loop controls systems and the providing of force information to the user may then take place concurrently. In particular, in 802, the determined joint torque values are used in their respective closed-loop control systems, for example, as described in reference to blocks 301-310 of FIG. 3, while in 803, at least one of the torque values is processed to generate force information for the tool, and in 804, the force information is provided to the user of the telesurgical system in a manner so as not to significantly affect the stability of the joint closed-loop control systems.

Figure 9:
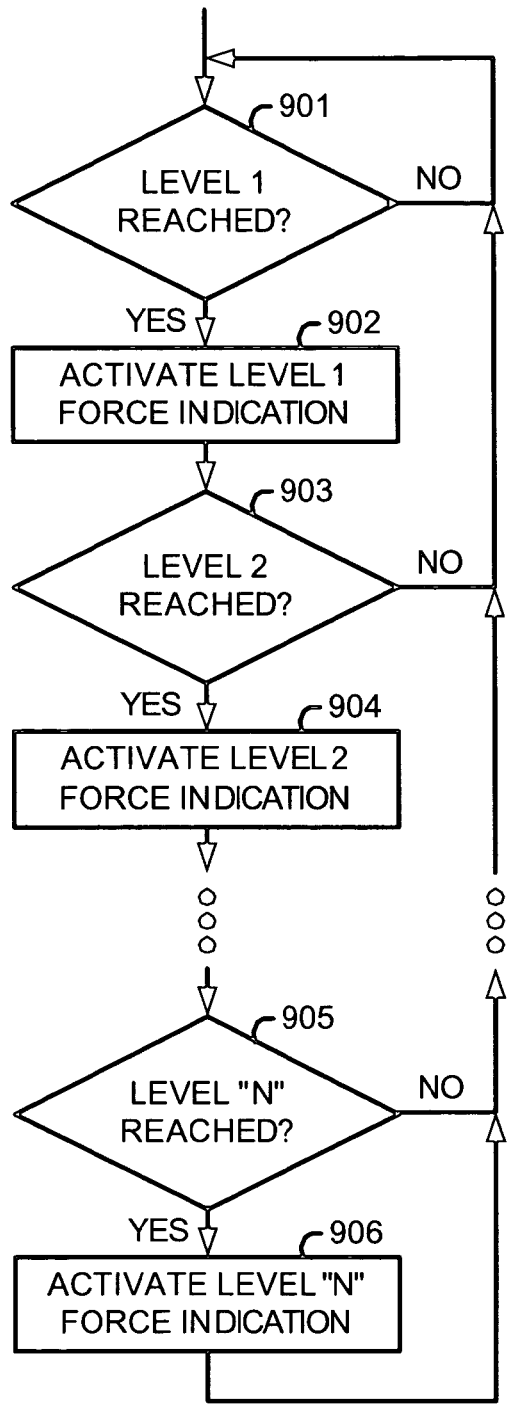
FIG. 9 illustrates a flow diagram of a method for providing force information to a user of a telesurgical system with escalating warnings.

Although the processing function 208 of the telesurgical system 200 is shown as being a simple gain and/or filter in corresponding blocks of FIGS. 3-6, it is to be appreciated that the processing may take on additional sophistication such as illustrated in FIG. 9. In particular, as shown in that figure, various force indications may be activated as the static force asserted on the tool increases. At each level, the force indication may be a different color or intensity as described previously herein, or it may be a different modality. For example, the level 1 force indication may be a user-visible indication, the level 2 force indication may be a user-audible indication, and the level 3 force indication may be a tactile sensation on the master manipulator 108. As in the cases of the slave controller 203 and the master controller 207, the processing function 208 is also implemented in a processor such as the processor 101 in the MIRS system 100.

A method and system whereby auxiliary information related to a surgical procedure to be performed by the system 100 can be selectively displayed on the viewer 106, together with an image of the surgical site captured by the endoscope 112, so as to enable the surgeon selectively to reference such information on the viewer 106 during the performance of the surgical procedure, in accordance with the invention, will now be described.

By displaying auxiliary information related to the surgical procedure in the image of the surgical site displayed at the viewer 106, the surgeon is able to reference such information without having to look at another source or display. For example, by displaying a patient's ECG signal in the image together with the image of the surgical site captured by the endoscope 112, the surgeon need not transfer his direction of view to a location removed from the image of the surgical site. This enables the surgeon to perform the surgical procedure with greater ease and confidence and with less distraction. Furthermore, the surgeon can prepare preoperative information specific to the surgical procedure to be performed, or specific to the patient on which the surgical procedure is to be performed, so as to enable the surgeon selectively to access such specific auxiliary information in the displayed image during the performance of the actual surgical procedure. When displaying the auxiliary information together with the image of the surgical site captured by the endoscope is referred to in this specification, such a description is to be interpreted to have a wide meaning including, for example, displaying the image in a discrete window overlaid on the image of the surgical site, displaying the auxiliary information so as to be merged with the image of the surgical site, such as merging a preoperative x-ray image with the image of the surgical site so that the surgeon can view hidden detail of the surgical site, displaying the auxiliary information selectively on the viewer instead of the image of the surgical site so that the surgeon is presented with an unobstructed view of the surgical site when performing the surgical procedure, the auxiliary information then being selectively displayable in the image at the viewer alternately with the image of the surgical site, and the like. It will be appreciated that the auxiliary information can be displayed on a separate image display or viewer where appropriate.

Figure 10:
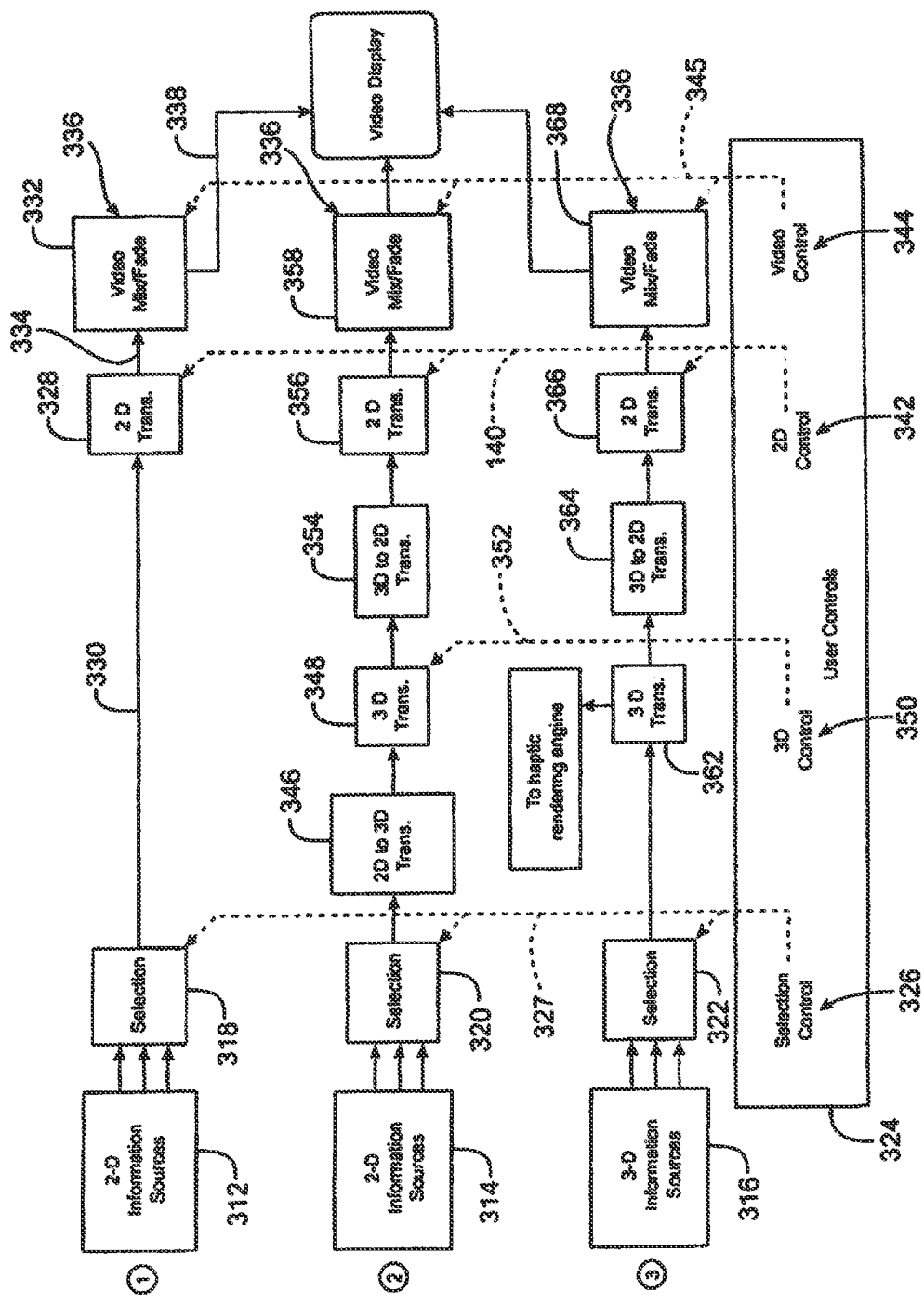
FIG. 10 illustrates a block diagram including components for providing auxiliary information related to a surgical procedure to be performed by a telesurgical system so as to be selectively displayable on a viewer together with an image of a surgical site.

Referring to FIG. 10 of the drawings, a plurality of sources of two-dimensional information is generally indicated by reference numeral 312. Another plurality of sources of two-dimensional information is generally indicated by reference numeral 314.

The sources of two dimensional auxiliary information at 312 define auxiliary information to be displayed in the image at the viewer 106 and which is of a type which, when displayed in the image, is to be adjustable to vary its displayed position relative to the image of the surgical site captured by the endo scope. The imaged information from 312 is typically adjustable relative to the image of the surgical site in two dimensions only. Accordingly, the position of the imaged information can be varied to change its position across the image of the surgical site.

If the imaged information from 312 is displayed in a window overlaid on the image of the surgical site, the size of the window is typically also adjustable in two dimensions. The types of information selectively accessible from the sources 312 include, for example, a prerecorded streaming video of the surgical procedure to be performed so that the operator can follow the procedure as depicted in the video while displayed in the image at the viewer 106 together with the image of the surgical site. The types of information can further include, for example, a real time ECG signal so that the surgeon can monitor the patient's heart beat within the displayed image at the viewer 106.

Another type of auxiliary information can be in the form of a previously captured and stored image from the endoscope of the surgical site, wherein the pre-captured image was taken to provide a generally panoramic view of the surgical site and the surrounding scene. Such a pre-captured panoramic image can be obtained by the endoscope 112. In such a case, the image can be captured when the viewing end of the endoscope 112 is relatively far removed from the surgical site. After the panoramic image or view is captured in this fashion, the endoscope can be moved such that its viewing end is closer to the surgical site so as to obtain a more suitable real time image for use in the performance of the actual surgical procedure.

It will be appreciated that images other than a panoramic image of the surgical site and surrounding scene can be provided for selective reference on the image display at the viewer 106. Such other images can include, for example, generic or patient specific anatomical images for aiding the operator, or surgeon, for example, in identifying structures so as to determine the surgical site location relative to the patient anatomy. Furthermore, such images can include, for example, images showing the location of the entry ports, or incision points, the position of the surgical instrument shafts and/or the end effectors so as to provide the operator with visible information relating to the location of surgical instruments or parts thereof. Such image can be computer generated where appropriate, or can be obtained from additional image capture devices, and/or the like. This can be useful to avoid collisions between the instrument shafts, for example. Furthermore, this can provide the operator with visible information enabling him to perceive how the instruments are interacting with each other and/or the patient, in addition to the real time image of the surgical site used to perform the actual surgical procedure. When this information is selected, the auxiliary information can be displayed, where appropriate, to surround or abut a generally closer view of the surgical site captured continually, or in real time, by the endoscope and which is used by the surgeon to monitor and control the surgical procedure. In this manner the surgeon, or operator, can be provided with the real time image from the endoscope at a preferably generally centrally disposed location in the viewed image, while the pre-captured, or real time, auxiliary image, e.g., a more panoramic view of the surgical site and surrounding scene, is displayed along the periphery of the real time image obtained from the endoscope 112. This can serve to provide the operator with a better idea of where he or she is operating relative to the area surrounding the surgical site. Instead of providing the auxiliary image to surround the real-time image of the surgical site, the auxiliary image can be displayed in a discrete window, or in a "picture in picture" arrangement, extending over the image of the real-time surgical site image. As another alternative, the auxiliary image can be displayed alternately with the actual real-time image. Thus, during the performance of a surgical procedure the surgeon can intermittently switch between the image of the real-time surgical site image and the auxiliary image by means of any appropriate switching input device or method, such as, buttons, switches, voice command, and/or the like. When the information from 312 is displayed in a window overlaid on the image of the surgical site, the surgeon can typically vary the size of the window and place the window relative to the image of the surgical site so that the information is presented at a location which is comfortable to the surgeon and at which the window does not obstruct important detail of the surgical site image.

By way of example, a specific application of such a "picture in picture" arrangement will now be described. During the course of a surgical procedure, the displayed image of the surgical site is typically in the form of a "narrow" field of view image normally being live, e.g., continually updated, magnified and focused particularly on the surgical site. Such a "narrow" field of view typically provides the operator with a large image of a relatively small area in the patient. Such a "narrow" field image is typically captured in real time by means of the endoscope 112. It has been found advantageous to provide the operator with a "wide angle" image of the surgical site and surrounding scene, to assist the operator in determining where the surgical site and surgical tools are with reference to the surrounding scene. Such a "wide angle" image can be in the form of a "still" image captured by the same endoscope at a position further removed from the surgical site than at which it is normally positioned when capturing the real time image used by the operator as he or she performs the surgical procedure. Instead, the "wide angle" image can be captured in real time by another image capture device, or endoscope, or the like. The two images can be displayed in a variety of different ways. In one way, the "wide angle" image can be displayed in a "smaller" window and the "narrow" field image can be displayed over a relatively larger area. The surgeon can then refer to the "smaller" window for referencing orientation, or the like. In another way, the "narrow" field image is displayed in a "smaller" window and the "wide angle" image is displayed over a relatively "larger" area to provide context to the surgeon to help him or her to remain oriented at the surgical site.

It can happen that the surgeon wishes to change the image displayed on the viewer 106. This can be achieved, e.g., by rotation of the endoscope 112 relative to the site viewed. Where the "wide angle" image is a "still" image, this image can be caused to rotate together with rotation of the "live", magnified image. This can be achieved by causing the "still" image to be modified, for example, by means of computer control, so that the "still" image rotates to the same degree as the "live" image, so as to maintain, for example, context for the surgeon should the surgeon desire to rotate the endoscope during surgery. In addition, or instead, if the surgeon desires to pan with the endoscope, the "still" image can be modified so that the "still" image preserves alignment, or registration, with a corresponding part of the "live" image.

The sources of two dimensional auxiliary information at 314 define auxiliary information to be displayed in the image at the viewer 106 and which is of a type which, when displayed in the image, is to be adjustable to vary not only its two-dimensional displayed position relative to the image of the surgical site captured by the endoscope, but also its displayed orientation in three dimensions relative to the displayed image of the surgical site. One of the sources at 314 can contain preoperative information which is to be aligned or brought into register with the image of the surgical site. For example, a two dimensional CAT scan image of a surgical site particular to the patient on which the surgical procedure is to be performed can be obtained preoperatively and loaded into one of the sources at 314. Such a preoperative image can be obtained so as to correspond with an image to be captured by the endoscope, in other words, an image corresponding to the image which the endoscope is to capture during the surgical procedure from a specific vantage point. Instead, the preoperative image can be from a vantage point different to that of where the endoscope is to be during the surgical procedure. During the surgical procedure, the surgeon can then access the CAT scan information from the particular source at 314 and place it in the displayed image of the surgical site. Such an image can then be adjusted in three dimensions so as to bring the preoperative CAT scan image generally into register with the image of the actual surgical site captured by the endo scope. Since the information from the sources 314 represent two dimensional information, there may be a limit to the amount of orientation change that can be tolerated before the information ceases to be of use to the surgeon.

Still referring to FIG. 10 of the drawings, a plurality of sources of three-dimensional information is indicated at 316. One of the sources can include, for example, a three-dimensional model corresponding to a surgical site on which a surgical procedure is to be performed. Such a three-dimensional model can be, for example, raw volumetric images, such as point cloud or voxel representations, or the like, a computer generated three-dimensional model or image, a segmented three-dimensional model obtained from CAT (Computer Aided Tomography) scans, MRI (Magnetic Resonance Imaging) techniques, or the like. During the surgical procedure, the surgeon can then access the model and place it in the image of the surgical site. The image corresponding to the auxiliary information in the form of the three-dimensional model, can typically be superimposed, or merged, with the image of the surgical site. The brightness of the image of the three-dimensional model is typically adjustable so as to cause it selectively to fade relative to the actual image of the surgical site.

Once placed in the image, the image of the model can be positionally and orientationally adjusted, and typically scaled, so as to enable the surgeon to bring the preoperative image into register with the actual image of the surgical site. Should the position of the endoscope be changed, for example, to obtain an image of the surgical site from a different vantage point, the registration of the preoperative image can be made to remain in register with the surgical site. This can typically be accomplished by causing the control system of the surgical system 100 to fix the position of the preoperative image relative to a suitable reference frame once the surgeon has brought the preoperative image generally into register in the displayed image. A suitable reference frame can be, for example, a reference frame attached relative to the patient, or the like. Since registration is often effected visually by the surgeon, it may be that the registration is not entirely true or accurate. Thus, should the endoscope position be moved to capture an image of the surgical site from a different vantage point, it may be that the surgeon may again have to perform a slight adjustment to the registration should the preoperative image not be correctly registered with the actual image of the surgical site upon changing the endoscope position. Instead of manual registration as described above, automatic registration of the preoperative image with the surgical site image can be achieved in accordance with known imaging techniques. Advantageously, registration can be accomplished by enabling the surgeon, or operator, to perform an initial manual registration procedure, followed by an automatic registration procedure in accordance with conventional methods to achieve a truer registration. Although reference has been made to a model, it will be appreciated that other auxiliary information can be used instead. Such other auxiliary information can include preoperative images as well as inter-operative images. For example, an inter-operative image, or preoperatively obtained model, and/or the like, of a beating heart can be registered with the actual image of the beating heart as captured by the endoscope, and/or the like.

Referring again to the two-dimensional information at the sources 312, the two dimensional information can typically be in the form of intrinsically two-dimensional information. Such information can include two dimensional visual images, such as video images, x-ray images, ultrasonic images, and/or the like. These two-dimensional images can be in digital or analog format, or the like. The information can be in the form of static images. Such static images can be in tiff, jpeg, and/or the like, file formats, for example. The information can be in the form of moving images, such as, for example, streaming videos, as already mentioned. Such moving images can be in mpeg, digital video, analog video, such as NTSC or PAL, and/or the like, formats, for example. The information can be textual, numeric, symbolic, and/or graphic in form. For example, the information sources can include sources of information in the form of words, numeric readouts, status icons, bargraphs, stripchart displays, and/or the like. In this manner, for example, representations of blood pressure gauges, heartbeat rate, warming messages, notifications, warning lights, warning icons, or other warning signals related to system status, for example, the time in the form of a representation of a digital or analog clock, e-mail messages, and/or the like, can be displayed. Accordingly, numeric readouts can correspond to blood pressure, heartbeat rate, elapsed and absolute time, and/or the like. Status icons can include icons indicating the status of the system 10, the identification of the type of surgical instruments currently mounted on the robotic arms, and/or the like. Bar graphs can correspond to patient specific information, such as, temperature, oxygen levels in the patient's blood, and/or the like. Bar graphs can also correspond to system specific information such as force magnitude, back-up battery status, and/or the like. Strip charts can correspond to EEG, ECG, blood pressure, and/or the like. Symbolic or graphic representations can correspond to clocks, warning indicators, and icons selectively activatable to provide access to sources of other auxiliary information, such as the three-dimensional and two-dimensional information, described above, menus, web pages and/or the like.

One, or more, of the sources may even comprise a separate computer operatively connected to the system 100. The computer can be a computer on which a surgeon has prepared preoperative information for a specific patient on which a surgical procedure using the system 100 is to be performed. Such a computer may be remote from the system 100. When linked to the system 100 as a source of auxiliary information, in accordance with the invention, the surgeon is able to access such preoperative information on the remote computer from the system 100, so as selectively to display such information on the viewer 106 during the performance of the surgical procedure. Thus, the surgeon, from this source, can access information which may be resident on a computer screen within his or her office, for example.

The images derived from the sources at 312, 314 and/or 316, may be stored images or may be real-time images. Accordingly, the system 100 may include dedicated memory on which the images can be recorded preoperatively if the images are patient or surgical site specific, for example, so as to be stored in resident memory of the system 100. Instead, or in addition, the system 100 can have one or more input connectors, or jacks, to enable the system 100 to be operatively linked to a source of auxiliary information external to the system 100. In this fashion, the system can be linked to an external source of auxiliary information, such as, for example, a remote computer as described above, an ECG source, computer networks such as Local Area Networks (LANS), the internet, and/or the like. Accordingly, it will be appreciated that the sources 312, 314 and 316, can be in the form of resident memory of the system 100, on which memory the auxiliary information is stored, or can be in the form sources external to the system 100, which external sources are connectable to the system 100 through the input connectors or jacks.

Sources of three-dimensional information are indicated at 316. These sources represent information which is intrinsically three-dimensional. Such types of information can include, for example, segmented organ and/or vasculature models, patient specific and/or generic biomedical models, non-biological geometric shapes, markers, and/or the like. Such types of information can also include, for example, real time three-dimensional video, laser scans, and/or the like. Such types of information can yet further include landmarks, identifiers, or other markers that are attached to fixed locations in space. The use of such landmarks, identifiers, or other markers will now be described, by way of example. In the case where the surgeon wishes to perform an anastomosis, for example, he or she can place a landmark, or identifier, or the like in the image displayed on the image display and then move the landmark or marker to correspond with the area where the anastomosis is to be performed. The marker can then be attached to the area so that if the endoscope is moved, for example, the marker remains in a registered condition with the area to which it is attached.

The non-biological geometric shapes are typically used to place visible haptic constraints in the displayed image at the viewer 106. The purpose of placing such haptic constraints in the image is, for example, to inhibit the end effectors from moving beyond such constraints, containing end effector movement within such constraints, and/or the like. Accordingly, the operator of the system can select an appropriately shaped geometric shape, or shapes, and, place it, or them, in the image, and then position the selected geometric shape, or shapes, in the image around an area, or organ, or tissue, for example, so as to protect that area, or organ, or tissue from invasion by the end effectors 110, or to constrain end effector movement to remain within such shape or shapes, miter-box-fashion. Thus, should the site on which it is desired to perform a surgical procedure be close to a sensitive organ, or tissue, or the like, an appropriately shaped geometric shape, or shapes, can be selected, placed in the scene of the surgical site and moved into a position in which the selected shape, or shapes, extend over the sensitive area. When the shape, or shapes, is so placed, a corresponding haptic constraint, corresponding to the selected and placed geometric shape, or shapes, is initialized so as to inhibit the end effectors 110 from trespassing beyond the visible constraint, or constraints, as placed in the image by the surgeon thereby to protect the sensitive tissue, or organ, or the like. The geometric shapes can be of any appropriate shape. Accordingly, such shapes can include, for example, polyhedral shapes, NURBS (Non-Uniform Rational B-Spline), implicit surface shapes, planar shapes such as walls, and/or the like. The geometric shapes can include volumetric shapes such as point cloud, voxcels, and/or the like. The file formats used to store such geometric shapes can be .obj, .dxf, .3ds, VRML, and/or the like, for example. It will be appreciated that once an appropriate selected geometric shape, or shapes, is placed in the image, the surgeon can move the shape, or shapes, into a position covering or shrouding an area of sensitivity. When this has been done, the control system of the system 100 can typically allocate coordinates to the placed shape, or shapes, relative to an appropriate frame, such as a frame attached to the patient, or the like. The system, after having determined the coordinates corresponding to the placed shape, or shapes, then inhibits the end effectors from moving beyond such coordinates or constrains end effector movement to remain within such coordinates. For a more detailed description of a control system of the system 100 whereby such constraints can be imposed, refer to U.S. application Ser. No. 09/288,068 filed Apr. 7, 1999 entitled "Aspects of a Control System of a Minimally Invasive Surgical Apparatus", now U.S. Pat. No. 6,493,608. Geometric shapes can also be used to guide the surgeon or to assist in finding locations of particular interest. Furthermore, haptic feedback can be used to indicate information about objects which may not be readily discernable visually. For example, sensitive areas can be given repulsive behavior so that the tools are not only inhibited from approaching the sensitive areas, but are restrained when approaching the sensitive areas at a predetermined distance from such areas.

Such geometric shapes can be provided with geometric description or additional information, and can contain information about appearance, e.g., via visual texture mapping, and/or the like, surface and volume properties, e.g., such as mass, density, impedance, and/or the like, in accordance with known methods in the field of haptics. The shapes can also be derived from biological sources such as segmented MRIs. Such additional information about geometric shapes can be used for visual representation, e.g., colors, patterns, textual maps, flashing appearances, and/or the like. Such additional information can also be used with haptic rendering to provide, for example, stiffness, artificial friction, masses, vibrations, or other physical or non-physical force cues. The various sources of information as indicated at 312, 314, and 316, are typically represented as icons on the display area of the video display 106. Accordingly, the operator of the system can select any one or more of the desired sources by selecting the appropriate associated icon. The step of selecting the desired source of auxiliary information is indicated by the blocks 318, 320, and 322 for the sources at 312, 314, and 316, respectively. Selection of a desired source typically takes place at the operator console C. Such selection can be made in any appropriate manner, such as by using buttons, foot pedals, a mouse, and/or the like, for example. Advantageously, such selection is made by making use of one, or both, or either of the master controls 108, 108. In such a case, one, or both, or either, of the masters 108, 108 can serve as a two-dimensional or three-dimensional mouse. Accordingly, one, or both, or either, of the masters can be arranged to perform functions relative to the displayed image in a manner analogous to a conventional mouse relative to a computer screen. Therefore, one, or both, or either, of the masters can be arranged to perform functions such as to point, highlight, move, select, and/or the like.

The masters each typically have at least six degrees of freedom of movement. Accordingly, when used as a three-dimensional mouse, such master can be arranged to control six variables, for example. Therefore, functions such as, shifting, rotating, panning, tilting scaling, and/or the like, can be performed simultaneously when one, or both, or either, of the masters are used as a three-dimensional mouse, without another input being required. In particular, for two-handed or two-master operation, any windows or overlays can be handled as "elastic" bodies, such that resizing, scaling, warping, and/or the like, can, for example, be controlled by pulling the masters apart, or the like. In this manner, the selected auxiliary information when displayed in the display image of the viewer 106 can be positionally and orientationally adjusted in three-dimensions in a three-dimensional environment, where appropriate, or where desired. The masters 108, 108 are typically provided with force feedback. The force feedback on the masters 108, 108 can be arranged to provide functions related to auxiliary information selection, placement, orientational and positional movement, for example, to draw, or "suck", the masters to an icon when an associated cursor is within a predetermined area around the icon, and/or the like. Refer to U.S. application Ser. No. 09/398,507, entitled "Master Having Redundant Degrees of Freedom," filed Sep. 17, 1999, now U.S. Pat. No. 6,714,839, the full disclosure of which is incorporated herein by reference, for further information in connection with master control. Whatever method and/or device used to make such selection, the selection step is indicated in the block 324 at 326 and as indicated by the dashed lines 327. It will be appreciated that the block 324 represents selection and regulation steps that are performed by means of the appropriate inputs, such as the master control devices 108, 108, at the surgeon's console C by the operator.

The steps whereby the information from the information sources 312 is selected and then presented or placed in the image at the video display will now be described in greater detail.

As mentioned, the selective placing of the auxiliary information from the sources 312 can be selectively caused to be displayed to extend at least partially across an image display area of the viewer 106, such as in a localized window. When displayed on the display area, the position at which the information is displayed relative to the display area can be regulated or changed by the operator in two dimensions. Once a desired source is selected by the operator by operation of an appropriate input at 326, the desired source is selected at 318. The information from that selected source is then forwarded to a two-dimensional transform indicated at 328, as indicated by arrow 330. After the two-dimensional transform step at 328, the information is fed to a video mix and fade step at 332, as indicated by arrow 334. At the block 332, the information from the selected source at 312 is mixed with the video image captured by the endoscope 112. The video image captured by the endoscope 112 is indicated by arrow 336. When the information from the selected source at 312 is thus mixed with the image captured by the endoscope 112, the combined images are forwarded to the video display as indicated by arrow 338 so that both images are placed in the image at the viewer 106.

Figure 11:
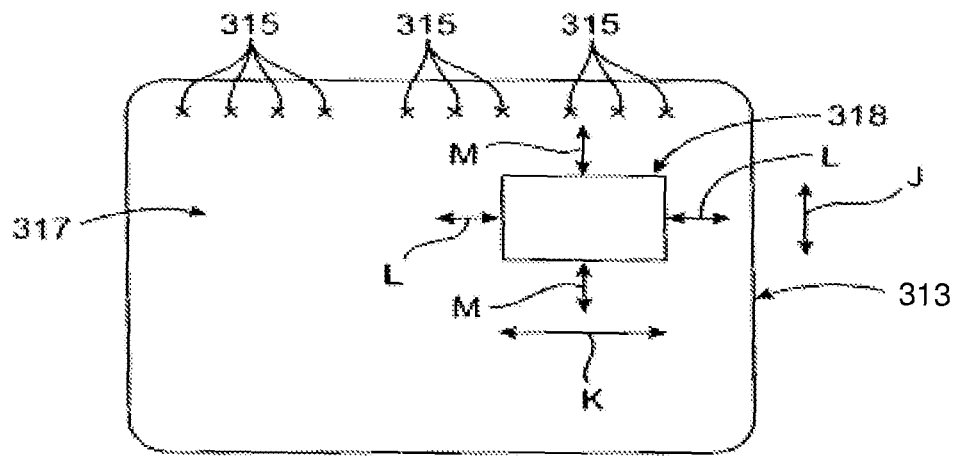
FIG. 11 shows a schematic view of an image of a surgical site displayed on the image display of the telesurgical system and further shows an image corresponding to auxiliary information from a selected source of auxiliary information displayed in a window overlaid on the image of the surgical site.

Referring to FIG. 11 of the drawings, an image comprising a combination or merger of the image from the endoscope and the selected source at 312 is indicated generally by reference numeral 313. An image derived from the source at 312 is indicated at 318, and is shown as being overlaid on the image from the endoscope indicated at 317. A row of icons is indicated by reference numerals 315. The source at 312 was selected by actuating a corresponding one of the icons 315.

Referring again to FIG. 10 and as indicated by the dashed line 140, the surgeon or operator of the system 100 can regulate the two-dimensional transform at 328, as indicated at 342. This can be achieved in any appropriate manner, such as through appropriate input devices such as, for example, buttons, toggles, joysticks, mice, and/or the like. Advantageously, one, or both, or either, of the master control devices 108, 108 are used as the input device or devices whereby the two-dimensional transform 328 can be regulated. The representation of the combined images can be presented such that the information from the selected source 312 is cropped in a localized window, as indicated in FIG. 11 of the drawings, in the image displayed at the viewer 106. Accordingly, the image 317 captured by the endoscope 112 is positioned to extend across at least a major part of the display area, the information from the selected source at 312 being positioned in a localized window overlaid on the image captured by the endoscope 112. By manipulation of the input at 342, the two-dimensional transform at 328 is regulated to cause the window displaying the information from the selected source at 312, to be moved relative to the rest of the image, and to be placed where desired by the operator, as indicated by arrows J and K in FIG. 11. Typically, the size of the window can be varied, as well as its position relative to the rest of the image, as indicated by arrows L and M.

The video mix and fade step 332 is also regulatable by, for example, the operator at the operator console C, or by another person, at a different location, if appropriate. An appropriate input for performing such regulation is indicated at 344 and is operatively connected as indicated by the dashed lines 345 to the video mix and fade block at 332. By manipulation of the input at 344, the information from the source at 312 can be faded relative to the image from the endoscope 112. Advantageously, the input at 344 is also performed by means of one, or both, or either, of the master controls 108, 108.

Referring now to the information sources at 314, these sources provide two dimensional information which, when displayed on the display area at the viewer 106, can be regulated so as to change the position of such information relative to the display area at the viewer in three dimensions, as described in greater detail herein below.

An appropriate one of the sources of two-dimensional information at 314 can be selected in similar fashion to the selection of one of the sources at 312. Accordingly, the operator can select information from a desired source at 314 by manipulating the appropriate input at 326. The selection step is indicated at 320. Once selected, the information from the desired source is forwarded to a two-dimensional to three-dimensional transform indicated at 346. At the step 346, the two-dimensional information from the selected source at 314 is converted to a three-dimensional representation. It is then passed through the three-dimensional transform indicated at 348. The three-dimensional transform at 348 is regulatable by the operator as indicated at 350 and by the dashed line 352. This can typically be achieved by means of any one or more of the inputs mentioned above. However, advantageously, the appropriate input is one, or both, or either, of the master controls 108, 108. By means of the input at 350, typically the position, orientation and scale of the two-dimensional information from the selected source at 314, can be regulated to change its position, orientation and scale in three dimensions. It will be appreciated that, in this fashion, not only the position, but also the orientation of the two-dimensional image as displayed in the image as viewed at the viewer 106 can be changed.

Once the operator has regulated the two-dimensional information by means of the three-dimensional transform at 348, the information is passed to block 354, where the information is transformed from a three-dimensional representation into a two dimensional representation. The two-dimensional transform is indicated at 356. The two-dimensional transform is regulatable by the operator through the input 342 so as to change the position of the information, as displayed in the image at the viewer 106, in two dimensions. It will be appreciated that this corresponds to changing the position of the image of the auxiliary information from the source at 314 relative to the image of the surgical site. After regulation at 356, the information is passed to a video mix and fade block at 358, where it is mixed with the image from the endoscope 112 as indicated by arrow 336. As in the case with the video mix and fade block 332, the operator can cause the information to fade relative to the image captured by the endoscope 112 by means of the input at 344. The image 336 from the endoscope 112 is combined with the information from the selected source at 314 and is then forwarded to the viewer 106 to be displayed thereon.

Figure 12A:
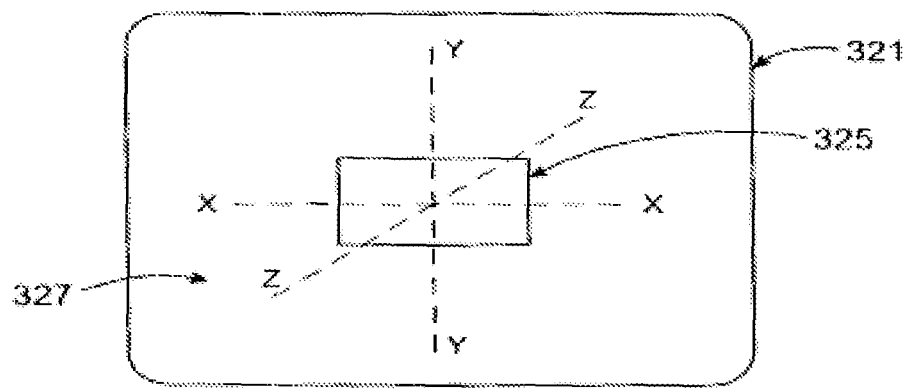
FIGS. 12A and B show schematic views illustrating the adjustment in position and orientation of an image corresponding to auxiliary information from a selected source of auxiliary information, relative to an image of the surgical site from an image capturing device.

Referring to FIG. 12A of the drawings, an image comprising a combination or merger of the image from the endoscope and the selected source at 314 is indicated generally by reference numeral 321. An image derived from the source at 314 is indicated at 323 and is shown as being overlaid on the image from the endo scope indicated at 327. As in the case with reference to FIG. 11, and as can best be seen in FIG. 12B of the drawings, the image from the source 314 can be repositioned with reference to arrows J and K and can be adjusted in size as indicated by arrows L and M. This is achieved by the operator of the system 100 at 342 by means of the transform at 356 as indicated by dashed line 140.

Figure 12B:
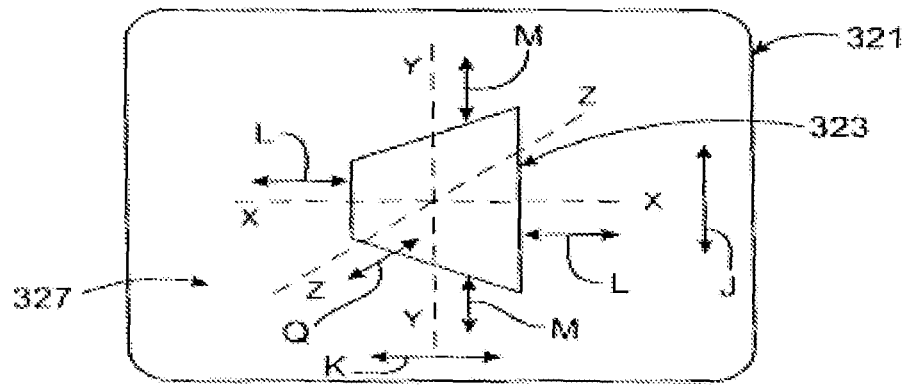

In addition, and with specific reference to FIG. 12B of the drawings, the image from the selected source at 314 is orientationally adjustable or regulatable. Accordingly, the image from the selected source 314 can be regulated so as to change its orientation in three dimensions with reference to the arbitrary reference frame indicated in dashed lines in FIG. 12A. Although in FIG. 12B the image from the source 314 is shown as having been adjusted angularly about an arbitrary y axis with reference to the reference frame in FIG. 12A, it will be appreciated that angular adjustment about the x and z axes can be performed in similar fashion. Such angular regulation of the image from the selected source at 314 is achieved by the operator of the system 100 at 350, so as to regulate the information from the selected source at 314 by means of the transform at 348 as indicated by dashed line 352. In similar fashion, the image can also be moved "inwardly" and "outwardly" as indicated by arrows Q along the z-axis.

Referring now to the three-dimensional information sources 316, information from one or more of the sources can be selected by the operator by means of the input 326 and as indicated by the block 322. The three-dimensional information from the selected source at 316 is then passed to a three-dimensional transform as indicated at 362. The operator, by using the input device at 350, can then regulate this information in the three-dimensional transform at 362 so as to vary typically the orientation, position and scale of an image derived from the selected source and as displayed at the viewer 106 in similar fashion as described above with reference to FIGS. 12A and 12B. Once the information has been regulated in this fashion, the information is forwarded to a block 364 where the three-dimensional information is transformed from three dimensions to two dimensions. The resultant two-dimensional information is then forwarded to a two-dimensional transform at 366. The information can then again be regulated by the operator by means of the input device at 342 as herein before described with reference to the two-dimensional transforms 328, 356. As before, the resultant information is then fed to a video mix and fade block as indicated at 368 where the information is mixed with the image from the endoscope and is then passed to the viewer. Where appropriate, the information can be caused automatically to register with a corresponding surgical site image captured by the endoscope as already described herein above. Instead, as described above, registration can be manual only, or a combination of manual and automatic methods.

It will be appreciated that the above methods can be used with two-dimensional single channel video display or with three-dimensional dual channel video display. In the latter case, the real time video source 336 can comprise two separate images for "right" and "left" channels for viewing by the right and left eyes of the surgeon. Elements 354 and 364 can then provide two separate images from two distinct viewpoints for the right and left channels respectively. The subsequent elements, or steps, can then be applied to both channels. Furthermore, element 328 can be arranged to duplicate the signal 334 into a left and a right channel and to shift them relative to each other to place the original two-dimensional image in a three-dimensional viewer at variable apparent depths.

Advantageously, at least one of the master controls is operatively arranged to fulfill some, preferably all, of the functions in the block 324. Accordingly, the operator need then not remove his hands from the master control devices 108, 108 when selecting and changing the position, orientation and scale of the auxiliary information when displayed in the image at the viewer 106. In this way, continuity of control of the surgical procedure is enhanced whilst still enabling the operator to access and place auxiliary information from one or more of the sources 312, 314 and 316.

As already mentioned, the masters 108, 108 are normally operatively associated with the slaves. Typically, when one, or both, or either, of the masters are to be used selectively to place an image corresponding to auxiliary information from a selected source 312, 314, 316 in the image or scene of the surgical site, the operative association between the master, or masters, and the slaves is temporarily interrupted. When this occurs, the slaves are typically held or locked in stationary positions at the surgical site. Accordingly, the slaves are locked in the positions they occupied immediately before disassociation with the masters 108, 108. The master or masters are then freed to enable them to be used to select and place the desired auxiliary information in the scene or image of the surgical site captured by the endoscope 112 and displayed across the display area of the image display or viewer 106. Once the auxiliary information has been selected and placed, operative association between the masters 108, 108 and the slaves is re-established to permit the operator to proceed with the surgical procedure with reference to the auxiliary information now displayed on the display area of the viewer 106 after having been selected and placed in the scene by means of one, or both, or either, of the masters 108, 108. Refer to U.S. application Ser. No. 09/398,960, entitled "Repositioning and Orientation of Master/Slave Relationship in Minimally Invasive Telesurgery," filed Sep. 17, 1999, now U.S. Pat. No. 6,459,926, the full disclosure of which is incorporated herein by reference, for a more detailed explanation of how the operative association between the masters and the slaves is preferably reestablished.

When one of the masters is used to select the desired auxiliary information, a cursor is typically generated in the image upon disassociation with the slaves. The cursor is then guided by movement of the master until the cursor is over the desired icon 315. The master is then also typically used to actuate the icon to cause the desired auxiliary information to be accessed and placed in the image of the surgical site. When placed, the master, or both masters, is then used to vary the position and/or orientation of the image corresponding to the selected auxiliary information relative to the image of the surgical site as described above, and where appropriate. One or both masters may be used to vary the position and orientation of auxiliary information, overlays and windows in a manner similar to the way in which masters are used to vary the position and orientation of an image from an image capture device. Of course, the present invention also encompasses other manners of manipulating auxiliary information, in addition to the preferred masters disclosed, such as by repositioning/rotating a joystick, using multiple input buttons to indicate the desired manipulation, or using a voice control/recognition system to command the system to manipulate the auxiliary information as desired.

Should, during the course of a surgical procedure, an image capture device generating a real time video image 336 be moved, the image displayed on the image display may be caused to shift and/or rotate in response to such image capture device movement. Instead, the video image 336 can be caused to shift/rotate electronically, for example. During such a change in the displayed real time image, the two-dimensional and three-dimensional transforms 328, 348, 354, 356, 362, 364, 366 can be arranged to synchronize their operation with the change in the displayed image so as to cause the auxiliary information to appear attached to the displayed real time image. Instead, the transforms can be arranged to ignore the change in the displayed real time image to cause the auxiliary information to appear attached to the image display and to drift relative to the changing real time image.

Figure 13:
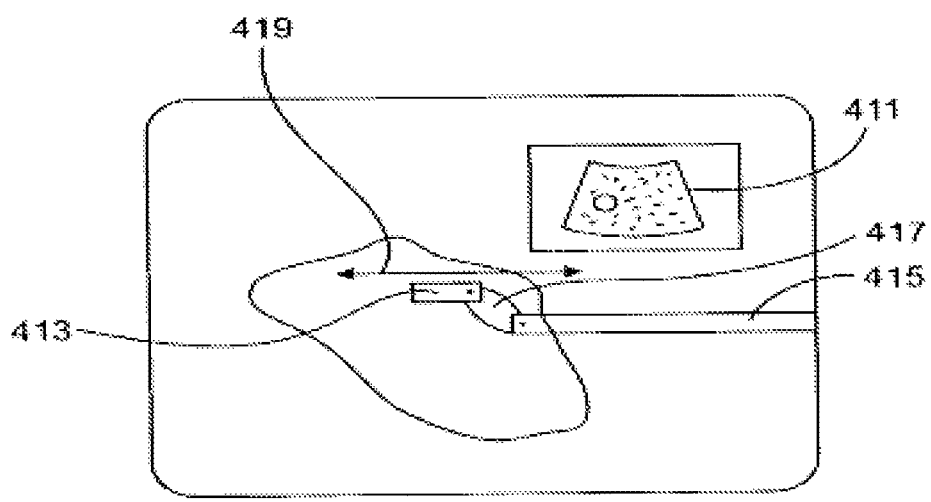
FIG. 13 shows a schematic diagram of an image displayed at a viewer, and further shows a probe gathering auxiliary information relating to a surgical procedure.

Another source of auxiliary information will now be described with reference to FIG. 13. Such a source of auxiliary information can typically include an appropriate image gathering device such as one including a transmitter and receiver arrangement, as schematically indicated at 413. An example of such a device is an ultrasound transducer which will be used by way of example only in the description which follows. Accordingly, the invention is not to be limited to an ultrasonic device. Any appropriate device which can gather similar information falls within the scope of the invention. Such a source can be used to obtain a preoperative or intraoperative two-dimensional or three-dimensional image, or model, corresponding to a surgical procedure to be performed. Accordingly, it can be either a two-dimensional source 312, 314 or a three-dimensional source 316 depending on its application. As a two-dimensional source, the ultrasonic transducer can be used to obtain a single ultrasound image. As a three-dimensional source it can be used to obtain a plurality of spaced ultrasonic images, or cuts, thereby to provide sufficient information for construction of a three-dimensional model. Accordingly, it can be arranged to move, or sweep, across a surgical site to capture such images, or cuts. This can typically be achieved, for example, in accordance with a pre-programmed sequence for moving the ultrasound transducer, manual movement of the ultrasound transducer, or the like. The ultrasonic transducer can be mounted at an end of a shaft to enable it to be introduced to the surgical site through a relatively small aperture, in a minimally invasive manner. The sweeping movement can be performed manually by moving an opposed end of the shaft positioned outside the body. To this end, a handle can be provided on the opposed end of the shaft. Conveniently, manually operable actuators can be provided at the handle to enable the ultrasonic transducer, or probe, to be moved relative to the end of the shaft on which it is mounted by manipulating the actuators. Instead, the shaft can be mounted on a robotic arm, the movement being controlled through a master control device. In another embodiment, the movement of the ultrasonic transducer can be controlled by means of a computer program. Accordingly, whether performed manually or automatically, a plurality of separate images can be obtained and used to form a "mosaiced" surface of images in a fashion similar to that known in the satellite and undersea imaging industries, namely, by "painting" the sensor, or ultrasonic transducer, across the surface being viewed. Said surface of images may be intrinsically two- or three-dimensional in nature depending on the movement of the sensor during the build-up of the image. A different series of image "slices" may be constructed from a sensor that produces a planar image and that is moved substantially normal to the image plane to produce a series of slices, as is known, for example, in prenatal ultrasonic imaging practice. Taken together, these form an intrinsically three-dimensional or volumetric image.

These built-up two- and three-dimensional images may then be introduced into the system to be selectively overlaid and positioned within the surgeon's field of view at the viewer. As can best be seen in FIG. 13, such an ultrasonic image, when in a two-dimensional format, may be displayed as indicated by reference numeral 411.

Such a source can also be used inter- or post-operatively. For example, it can be used as a flow probe, or the like, to enable the surgeon, for example, to ascertain the degree of fluid flow through a vessel, or the like. In such a case, when, for example, an anastomosis procedure has been performed, a surgeon, or operator, of the system may wish to determine whether or not the anastomosed vessels are allowing sufficient blood flow therethrough, whether or not one or more of the vessels has been damaged during the procedure so as to require further corrective surgery, and/or the like. The flow probe, or ultrasonic transducer, can then be used to establish this.

Advantageously, the ultrasonic transducer, or other appropriate device, or flow probe, can be mounted on an end of a shaft 415 to permit it to be introduced into a patient body in similar fashion to the surgical instruments 110, in a minimally invasive manner. The ultrasonic transducer 413 can be mounted on an end of the shaft 415 by means of the wrist member 417 to enable it to be angularly displaced relative to the shaft in multiple degrees of freedom of movement. The mounting of the ultrasonic device on the end of the shaft, whether by means of one or more wrist members, or otherwise, is preferably such as to provide the ultrasonic device with relatively large sweeping movement capability relative to the end of the shaft, as indicated by arrows 419. Accordingly, it can have a relatively large lateral range of motion although narrow ranges of motion, or none at all, relative to the end of the shaft, fall within the scope of the present invention. Movement of the ultrasonic device relative to at least the end of the shaft is preferably controlled from outside the patient body, in use. For example actuators positioned remote from the end on which the ultrasonic transducer is mounted may be used to control movement of the ultrasonic device relative to the end of the shaft from outside the patient body. Instead, or in addition, actuators can be provided to cause the ultrasonic transducer to scan an area of interest. The shaft may have a handle at its proximal end, opposed from the flow probe, for manual control by means of manually controllable actuators, or it may be mountable on a robotic arm as described above for control by means of a master control device. Accordingly, in a preferred embodiment, the ultrasonic device is mounted on a distal end of a robotic surgical tool of the type disclosed in U.S. Pat. No. 5,808,665, entitled "Endoscope Surgical Instrument and Method For Use," the full disclosure of which is incorporated herein by reference. Movement of the ultrasonic transducer across a desired area of interest could then be accomplished by a surgeon or operator of the system 100 by manipulation of a remotely controlled master control at the control station C as described in U.S. application Ser. No. 09/398,507. Instead, the probe could be arranged to be releasably grasped by a surgical instrument having an appropriate complimentary end effector.

Another application of the information gathered by such an ultrasound probe, or the like, is to collect preoperative data on the patient, at the surgical site, for example. Such preoperative data can then be used to determine a location of, for example, a stenosis, or blockage, or the like, in a blood vessel that is to be anastomosed during a heart bypass operation for example. The auxiliary information can then be overlaid on the "live" image of the surgical site to indicate to the surgeon where the surgeon should conduct the anastomosis. Conveniently, and as already described, markers or identifiers can then be attached to the location of the stenosis such that, should the displayed image be changed, such as, for example by moving the endo scope, the markers or identifiers remain in a registered condition with the stenosis so that the location of the stenosis remains clearly indicated in the displayed image.

Although the various aspects of the present invention have been described with respect to a preferred embodiment, it will be understood that the invention is entitled to full protection within the full scope of the appended claims.

We claim:

1. A robotic system comprising:
a display;
an ultrasound transducer;
a robotic arm mechanically coupled to the ultrasound transducer; and
a processor executing a pre-programmed sequence of computer instructions that causes the robotic arm to move the ultrasound transducer so as to sweep the work site during performance of a medical procedure on the patient to obtain a plurality of spaced two-dimensional ultrasound images to provide sufficient information for construction of a three-dimensional model of at least a portion of the work site.

2. The robotic system of claim 1, further comprising:
an endoscope for capturing video images of a work site in a patient;
wherein the processor is programmed to: computationally construct the three-dimensional model by using information of the plurality of spaced two-dimensional ultrasound images; and cause images derived from the video images captured by the endoscope of the work site and a graphical representation of the three-dimensional model constructed from the plurality of spaced two-dimensional ultrasound images captured by the ultrasound transducer to be concurrently displayed on the display.

3. The robotic system of claim 2,
wherein the processor is programmed to display the images derived from the video images captured by the endoscope in a picture section of the display and the graphical representation of the three-dimensional model within a picture-in-picture section of the display.

4. The robotic system of claim 2,
wherein the processor is programmed to spatially register ultrasound images captured by the ultrasound transducer with the images derived from the video images captured by the endoscope.

5. The robotic system of claim 1, further comprising:
a shaft coupled to the robotic arm; and
a wrist member coupling the ultrasound transducer to the shaft so as to facilitate movement of the ultrasound transducer relative to an end of the shaft.

* * * * *